(12) United States Patent
Parrott et al.

(10) Patent No.: US 10,709,431 B2
(45) Date of Patent: Jul. 14, 2020

(54) LAPAROSCOPIC DEVICES AND RELATED METHODS

(71) Applicant: Epic Medical Concepts & Innovations, Inc., Olathe, KS (US)

(72) Inventors: David Andrew Parrott, Cincinnati, OH (US); James Lucas, Olathe, KS (US)

(73) Assignee: Epic Medical Concepts & Innovations, Inc., Olathe, KS (US)

( * ) Notice: Subject to any disclaimer, the term of this patent is extended or adjusted under 35 U.S.C. 154(b) by 81 days.

(21) Appl. No.: 16/008,705

(22) Filed: Jun. 14, 2018

(65) Prior Publication Data

US 2018/0360434 A1     Dec. 20, 2018

Related U.S. Application Data

(60) Provisional application No. 62/519,427, filed on Jun. 14, 2017.

(51) Int. Cl.
  *A61B 17/00* (2006.01)
  *A61B 17/29* (2006.01)
(52) U.S. Cl.
  CPC ........ *A61B 17/00234* (2013.01); *A61B 17/29* (2013.01); *A61B 2017/0046* (2013.01);
  (Continued)
(58) Field of Classification Search
  CPC ................... A61B 17/2909; A61B 2017/2845
  (Continued)

(56) References Cited

U.S. PATENT DOCUMENTS

| 3,730,185 A | 5/1973 | Cook et al. |
| 3,888,004 A | 6/1975 | Coleman |

(Continued)

FOREIGN PATENT DOCUMENTS

| DE | 4300307 | 7/1994 |
| DE | 296 23 921 | 8/2000 |

(Continued)

OTHER PUBLICATIONS

European Search Report in European Application No. 13743092.2, dated Jun. 22, 2015, 5 pages.

(Continued)

*Primary Examiner* — Gregory A Anderson
*Assistant Examiner* — Alyssa M Keane
(74) *Attorney, Agent, or Firm* — Fish & Richardson P.C.

(57) ABSTRACT

A laparoscopic device includes an elongate shaft, an end effector coupled to a distal end of the elongate shaft, a rounded housing coupled to a proximal end of the elongate shaft and having a center point positioned along the central axis of the elongate shaft, and first and second cables extending from the end effector to the rounded housing respectively along first and second sides of the elongate shaft. The laparoscopic device also includes a handle that is adjustable between an expanded configuration and a compressed configuration. In the expanded configuration, the rounded housing can be rotated to further rotate a single shaft assembly with respect to the central axis of the elongate shaft, and the rounded housing can be pivoted to bend the end effector. In the compressed configuration, the rounded housing is fixed with respect to the handle.

19 Claims, 24 Drawing Sheets

(52) U.S. Cl.
CPC .............. *A61B 2017/00314* (2013.01); *A61B 2017/00407* (2013.01); *A61B 2017/00477* (2013.01); *A61B 2017/291* (2013.01); *A61B 2017/292* (2013.01); *A61B 2017/2903* (2013.01); *A61B 2017/2905* (2013.01); *A61B 2017/2946* (2013.01)

(58) Field of Classification Search
USPC ........................................................ 606/205
See application file for complete search history.

(56) References Cited

U.S. PATENT DOCUMENTS

| | | |
|---|---|---|
| 4,258,716 A | 3/1981 | Sutherland |
| 4,320,761 A | 3/1982 | Haddad |
| 4,439,649 A | 3/1984 | Cecchi |
| 4,672,964 A | 6/1987 | Dee et al. |
| 4,688,555 A | 8/1987 | Wardle |
| 4,763,669 A | 8/1988 | Jaeger |
| 4,838,853 A | 6/1989 | Parisi |
| 4,852,550 A | 8/1989 | Koller et al. |
| 4,861,332 A | 8/1989 | Parisi |
| 4,872,456 A | 10/1989 | Hasson |
| 4,877,026 A | 10/1989 | de Laforcade |
| 4,880,015 A | 11/1989 | Nierman |
| 4,940,468 A | 7/1990 | Petillo |
| 4,978,333 A | 12/1990 | Broadwin et al. |
| 4,986,825 A | 1/1991 | Bays et al. |
| 5,024,652 A | 6/1991 | Dumenek et al. |
| 5,026,387 A | 6/1991 | Thomas |
| 5,112,299 A | 5/1992 | Pascaloff |
| 5,133,736 A | 7/1992 | Bales, Jr. et al. |
| 5,166,787 A | 11/1992 | Irion |
| 5,174,300 A | 12/1992 | Bales et al. |
| 5,176,697 A | 1/1993 | Hasson et al. |
| 5,209,747 A | 5/1993 | Knoepfler |
| 5,224,954 A | 7/1993 | Watts et al. |
| 5,254,130 A | 10/1993 | Poncet et al. |
| 5,258,007 A | 11/1993 | Spetzler et al. |
| 5,275,615 A | 1/1994 | Rose |
| 5,281,220 A | 1/1994 | Blake, III |
| 5,282,806 A | 2/1994 | Haber et al. |
| 5,282,807 A | 2/1994 | Knoepfler |
| 5,282,826 A | 2/1994 | Quadri |
| 5,300,081 A | 4/1994 | Young et al. |
| 5,308,358 A | 5/1994 | Bond et al. |
| 5,314,445 A | 5/1994 | Heidmueller nee Degwitz et al. |
| 5,318,589 A | 6/1994 | Lichtman |
| 5,330,502 A | 7/1994 | Hassler et al. |
| 5,350,355 A | 9/1994 | Sklar |
| 5,350,391 A | 9/1994 | Iacovelli |
| 5,354,311 A | 10/1994 | Kambin et al. |
| 5,368,606 A | 11/1994 | Marlow et al. |
| 5,374,277 A | 12/1994 | Hassler |
| 5,383,888 A | 1/1995 | Zvenyatsky et al. |
| 5,403,342 A | 4/1995 | Tovey |
| 5,405,344 A | 4/1995 | Williamson et al. |
| 5,474,571 A | 12/1995 | Lang |
| 5,536,251 A | 7/1996 | Evard et al. |
| 5,743,456 A | 4/1998 | Jones |
| 5,817,119 A | 10/1998 | Klieman et al. |
| 5,827,323 A | 10/1998 | Klieman et al. |
| 5,882,294 A | 3/1999 | Storz et al. |
| 5,899,914 A * | 5/1999 | Zirps ................. A61B 17/1608 606/170 |
| 6,443,973 B1 | 9/2002 | Whitman et al. |
| 6,569,105 B1 | 5/2003 | Kortenbach et al. |
| RE38,335 E | 11/2003 | Aust et al. |
| 7,131,985 B1 | 11/2006 | Manhes |
| 7,156,846 B2 | 1/2007 | Dycus et al. |
| 7,250,027 B2 | 7/2007 | Barry |
| 7,481,824 B2 | 1/2009 | Boudreaux et al. |
| 7,988,699 B2 | 8/2011 | Martz et al. |
| 8,585,734 B2 | 11/2013 | Hallbeck et al. |
| 2003/0216752 A1 | 11/2003 | Williamson, IV et al. |
| 2003/0236549 A1 | 12/2003 | Bonadio et al. |
| 2004/0254573 A1 | 12/2004 | Dycus et al. |
| 2005/0187575 A1* | 8/2005 | Hallbeck ................ A61B 17/29 606/205 |
| 2006/0047303 A1 | 3/2006 | Ortiz et al. |
| 2006/0190027 A1 | 8/2006 | Downey et al. |
| 2007/0152014 A1 | 7/2007 | Gillum et al. |
| 2007/0276430 A1 | 11/2007 | Lee et al. |
| 2007/0282371 A1* | 12/2007 | Lee ...................... A61B 17/062 606/205 |
| 2009/0312605 A1 | 12/2009 | Hallbeck et al. |
| 2010/0030018 A1 | 2/2010 | Fortier et al. |
| 2010/0228235 A1 | 9/2010 | Lee et al. |
| 2011/0118707 A1 | 5/2011 | Burbank |
| 2011/0311936 A1 | 12/2011 | Marie-Catherine |
| 2012/0029517 A1 | 2/2012 | Tan |
| 2012/0109186 A1* | 5/2012 | Parrott ................. A61B 17/29 606/206 |

FOREIGN PATENT DOCUMENTS

| | | |
|---|---|---|
| EP | 0434793 | 7/1991 |
| EP | 0577423 | 1/1994 |
| EP | 0902652 | 7/1995 |
| EP | 0918 489 | 6/1999 |
| EP | 1366705 | 12/2003 |
| EP | 1709912 | 10/2006 |
| FR | 2681775 | 4/1993 |
| WO | WO 1991/02493 | 3/1991 |
| WO | WO 1993/07816 | 4/1993 |
| WO | WO 1994/20034 | 9/1994 |
| WO | WO 2005/079333 | 1/2005 |
| WO | WO 2006/075153 | 7/2006 |

OTHER PUBLICATIONS

International Preliminary Report on Patentability in International Application No. PCT/US2013/024398, dated Aug. 14, 2014, 8 pages.

International Search Report and Written Opinion in International Application No. PCT/US2013/024398, dated Jun. 11, 2013, 10 pages.

International Search Report and Written Opinion in International Application No. PCT/US2018/37559, dated Aug. 28, 2018, 7 pages.

International Searching Authority, Written Opinion International Application No. PCT/US2005/004517, dated Nov. 7, 2007, 5 pages.

Microline Pentax, "Microline Announces the World's First Reposable Deflexable Instruments," 2009, 1 page.

Novare Surgical Systems, Inc., "EndoLink™ Articulating Instruments," 2005, 1 page.

Novare Surgical Systems, Inc., "RealHand High Dexterity (HD) instruments," Oct. 7, 2009, 1 page.

Veelen, "Handle for laparoscopic instrument," Medisign Delft Program for research and development of products in Healthcare,: Aug. 20, 1999, 1 page.

* cited by examiner

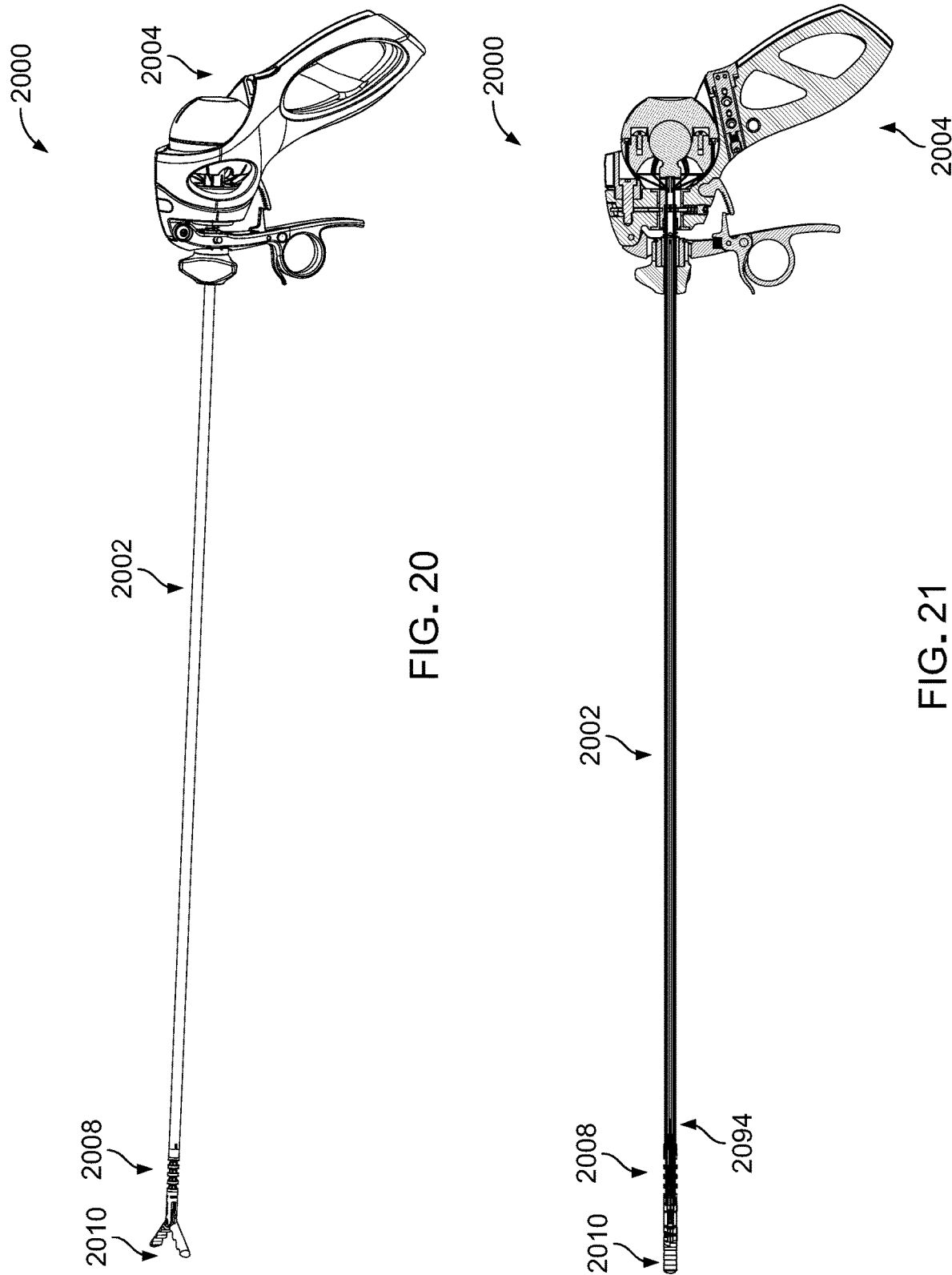

LAPAROSCOPIC DEVICES AND RELATED METHODS

CROSS-REFERENCE TO RELATED APPLICATIONS

This application claims priority to U.S. Provisional Patent Application No. 62/519,427, filed on Jun. 14, 2017, the entire contents of which are incorporated herein by reference.

TECHNICAL FIELD

This disclosure is directed to laparoscopic devices and related methods.

BACKGROUND

Laparoscopic surgery is a type of minimally invasive surgery in which procedures are performed through a small opening (e.g., an incision or a natural body orifice) in the body. For example, a trocar may be implanted within the opening, and small tools may be inserted though the trocar thereafter to perform a desired procedure within an insufflated body cavity. Laparoscopic tools are often difficult to use due to their small size and sub-optimal design. In some circumstances, inadequate laparoscopic tools may cause undue fatigue or harm to the surgeon, further complicating a procedure. Surgery outcomes may be improved and physical challenges (e.g., visualization and hand fatigue) of surgeons may be alleviated with improved designs of laparoscopic tools.

SUMMARY

In general, this disclosure relates to an ergonomic laparoscopic device that is designed for performing laparoscopic surgical procedures within a body cavity of a patient. The laparoscopic device includes a trackball, a trigger mechanism, a cable system, and a robust handle body that together provide multiple functions, including opening and closing of an end effector, locking and unlocking (e.g., releasing) of an open/closed configuration of the end effector, articulation of the end effector, locking and unlocking of an articulated configuration of the end effector, rotation of a shaft assembly, and removal and installation of the shaft assembly with respect to a handle. Accordingly, a user can manipulate the laparoscopic device to perform one or more of these functions to carry out a laparoscopic procedure. Furthermore, the laparoscopic device can exhibit more than one configuration respectively associated with these functions at the same time due to couplings among the component parts of the laparoscopic device, even while the functions can be executed independently of one another.

In one aspect, a laparoscopic device includes an elongate shaft, an end effector coupled to a distal end of the elongate shaft, a rounded housing coupled to a proximal end of the elongate shaft, translatable along a central axis of the elongate shaft, and having a center point positioned along the central axis of the elongate shaft, and first and second cables extending from the end effector to the rounded housing respectively along a first side of the elongate shaft and along a second side of the elongate shaft disposed opposite the first side. At a first axial position, the rounded housing is rotatable about any axis intersecting the center point of the rounded housing to move the first and second cables axially in opposite directions along the central axis of the elongate shaft to bend the end effector with respect to the central axis of the elongate shaft. At a second axial position, the rounded housing is rotatable in fixed relation to the elongate shaft, the first and second cables, and the end effector to rotate the elongate shaft, the first and second cables, and the end effector together as a single shaft assembly with respect to the central axis of the elongate shaft and with any orientation of the end effector with respect to the central axis of the elongate shaft.

Embodiments may include one or more of the following features.

In some embodiments, the laparoscopic device further includes a bendable segment that couples the elongate shaft to the end effector.

In certain embodiments, the bendable segment includes multiple ball-and-socket joints.

In some embodiments, the laparoscopic device further includes a rod that extends from the proximal end of the shaft to the end effector and that is configured to effect opening and closing of the end effector based on axial movement of the rod.

In certain embodiments, the rod includes a compliant portion that passes through the bendable segment such that an open or closed configuration of the end effector is independent of the orientation of the end effector with respect to the central axis of the shaft and independent of a rotational orientation of the single shaft assembly.

In some embodiments, the laparoscopic device further includes an interior ball about which the rounded housing is rotatable.

In certain embodiments, the interior ball is translatable along the central axis of the elongate shaft to allow the rounded housing to move between the first and second axial positions.

In some embodiments, the rounded housing is biased to the second axial position.

In some embodiments, the laparoscopic device further includes a brake that prevents rotational movement of the rounded housing with respect to the central axis of the elongate shaft when the rounded housing is in the second axial position.

In certain embodiments, the rounded housing is disengaged from the brake when the rounded housing is in the first axial position.

In some embodiments, the rounded housing includes a visible feature that indicates an orientation of the end effector with respect to the central axis of the elongate shaft.

In certain embodiments, the laparoscopic device further includes multiple additional cables.

In some embodiments, the laparoscopic device further includes a handle assembly.

In certain embodiments, the laparoscopic device further includes a collar that is fixedly coupled to the proximal end of the elongate shaft and by which the single shaft assembly, as a unit, can rotate with respect to the handle assembly.

In some embodiments, the collar is releasably coupled to the handle to disengage the single shaft assembly, as the unit, from the handle assembly.

In certain embodiments, the handle assembly includes a ratcheting mechanism by which an open or closed configuration of the end effector can be locked and unlocked.

In another aspect, a method of using a laparoscopic device that includes a shaft, a trackball, and an end effector includes translating the trackball distally to a first axial position along a central axis of the shaft, rotating the trackball to articulate the end effector while the trackball is disposed at the first axial position such that the end effector achieves an articulated configuration with respect to the central axis of the shaft, translating the trackball proximally to a second axial position along the central axis of the shaft while the end effector is in the articulated configuration, and rotating the trackball, the shaft, and the end effector together as a single shaft assembly while the trackball is disposed at the second axial position and while the end effector is in the articulated configuration.

Embodiments may include one or more of the following features.

In some embodiments, the method further includes locking the articulated configuration of the end effector with respect to the central axis of the shaft.

In certain embodiments, the method further includes rotating a trigger of the laparoscopic device to change a degree to which the end effector is open and adjusting a ratchet mechanism of the laparoscopic device to lock the degree to which the end effector is open.

In some embodiments, the method further includes disengaging the single shaft assembly from a handle assembly of the laparoscopic device.

In another aspect, a laparoscopic device includes an elongate shaft, an end effector coupled to a distal end of the elongate shaft, a rounded housing coupled to a proximal end of the elongate shaft and having a center point positioned along the central axis of the elongate shaft, and first and second cables extending from the end effector to the rounded housing respectively along a first side of the elongate shaft and along a second side of the elongate shaft disposed opposite the first side. The laparoscopic device also includes a handle that is adjustable between an expanded configuration and a compressed configuration. In the expanded configuration of the handle, the rounded housing can be rotated in fixed relation to the elongate shaft, the first and second cables, and the end effector to rotate the elongate shaft, the first and second cables, and the end effector together as a single shaft assembly with respect to the central axis of the elongate shaft, and the rounded housing can be pivoted to bend the end effector with respect to the central axis of the elongate shaft. In the compressed configuration of the handle, the rounded housing is fixed with respect to the handle.

In some embodiments, the laparoscopic device further includes a bendable segment that couples the elongate shaft to the end effector.

In certain embodiments, the bendable segment includes multiple of ball-and-socket joints.

In some embodiments, the laparoscopic device further includes a rod that extends from the proximal end of the shaft to the end effector and that is configured to effect opening and closing of the end effector based on axial movement of the rod.

In certain embodiments, the rod includes a compliant portion that passes through the bendable segment such that an open or closed configuration of the end effector is independent of the orientation of the end effector with respect to the central axis of the shaft and independent of a rotational orientation of the single shaft assembly.

In some embodiments, the laparoscopic device further includes an interior ball about which the rounded housing is rotatable.

In certain embodiments, the interior ball and the rounded housing together form a track ball assembly.

In some embodiments, the laparoscopic device further includes a collar that extends from the interior ball and that is rigidly attached to the proximal end of the elongate shaft to couple the rounded housing to the elongate shaft.

In certain embodiments, the handle includes a central portion and two opposing outer portions that can be compressed towards the central portion to place the handle in the compressed configuration.

In some embodiments, the laparoscopic device further includes multiple additional cables.

In certain embodiments, the single shaft assembly is separable from the handle.

In some embodiments, the handle includes a ratcheting mechanism by which an open or closed configuration of the end effector can be locked and unlocked.

In certain embodiments, the rounded housing is rotatable about any axis intersecting the center point of the rounded housing to move the first and second cables axially in opposite directions along the central axis of the elongate shaft to bend the end effector with respect to the central axis of the elongate shaft while the handle is in the expanded configuration.

In some embodiments, the rounded housing is rotatable to rotate the single shaft assembly with respect to the central axis of the elongate shaft with any orientation of the end effector with respect to the central axis of the elongate shaft while the handle is in the expanded configuration.

Other aspects, features, and advantages will be apparent from the description, the drawings, and the claims.

DESCRIPTION OF DRAWINGS

FIG. 20 is a perspective view of a laparoscopic device including an end effector in an open configuration.

FIG. 21 is a cross-sectional view of the laparoscopic device of FIG. 20.

DETAILED DESCRIPTION

Figure 1:
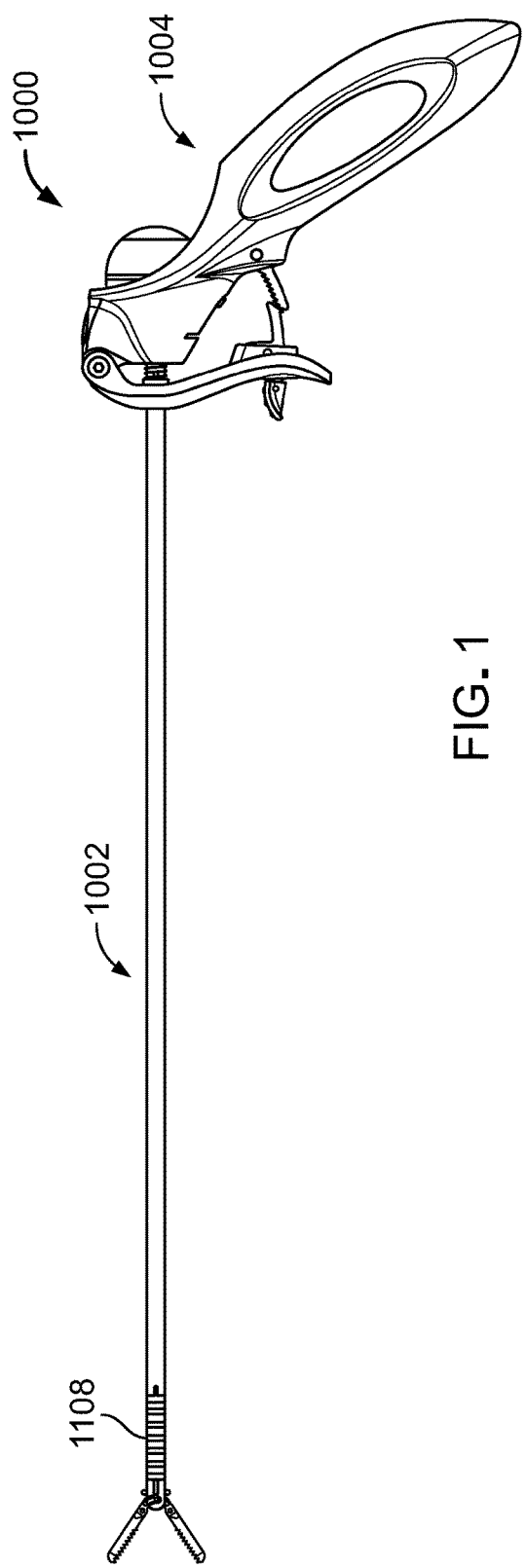
FIG. 1 is a side view of a laparoscopic device including an end effector in an open configuration.
Figure 2:
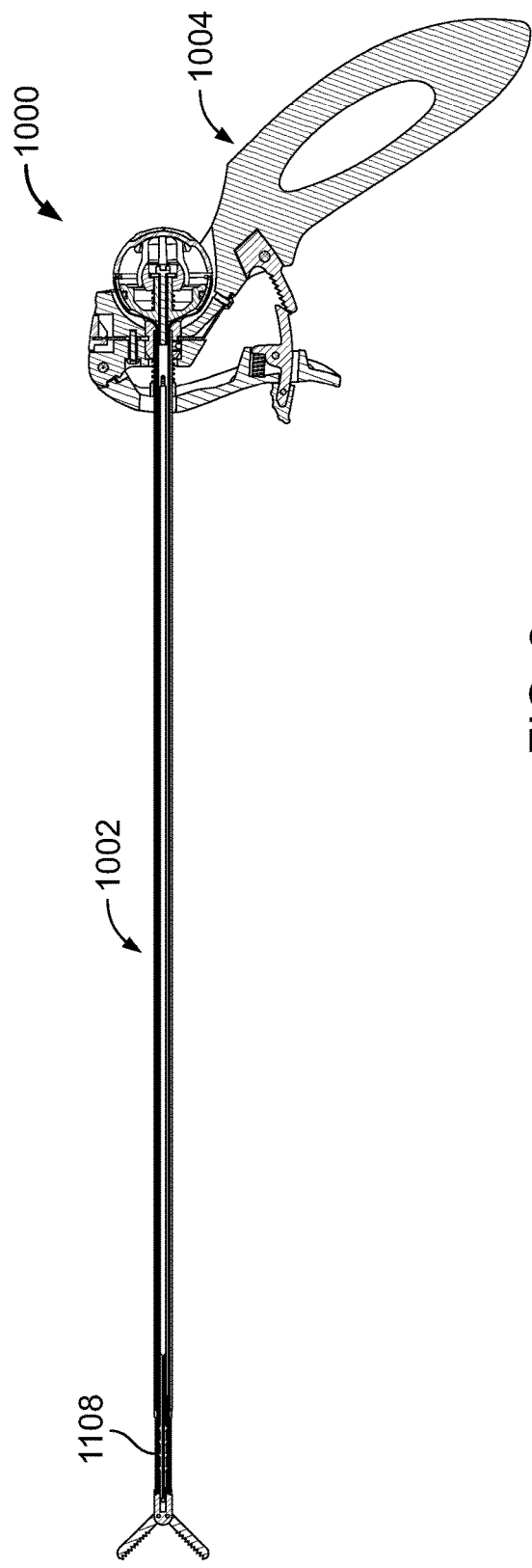
FIG. 2 is a cross-sectional view of the laparoscopic device of FIG. 1.
Figure 3:
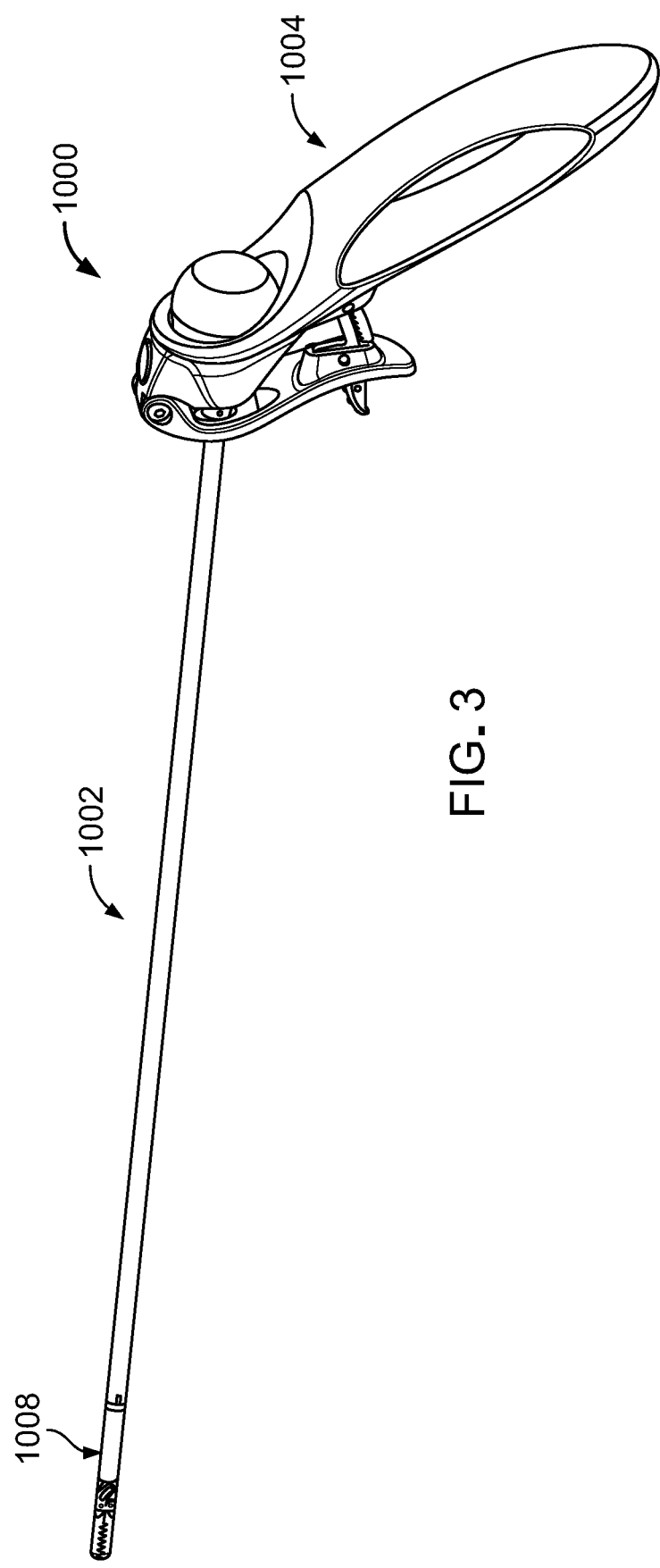
FIG. 3 is a perspective view of the laparoscopic device of FIG. 1 with the end effector in a closed configuration.

FIGS. 1-3 illustrate a laparoscopic device 1000 designed for performing laparoscopic surgical procedures within a body cavity (e.g., an abdominal cavity) of a patient. Example laparoscopic surgical procedures that can be performed using the laparoscopic device 1000 include gastric banding procedures, hernia repair procedures, arthroscopic procedures, and other single incision laparoscopic procedures. The laparoscopic device 1000 includes a shaft assembly 1002 that is constructed to manipulate tissues within the body cavity and a handle assembly 1004 that is coupled to the shaft assembly 1002 for manipulating the shaft assembly 1002. The shaft assembly 1002 is separable from the handle assembly 1004 and is rotatable with respect to the handle assembly 1004.

Figure 4:
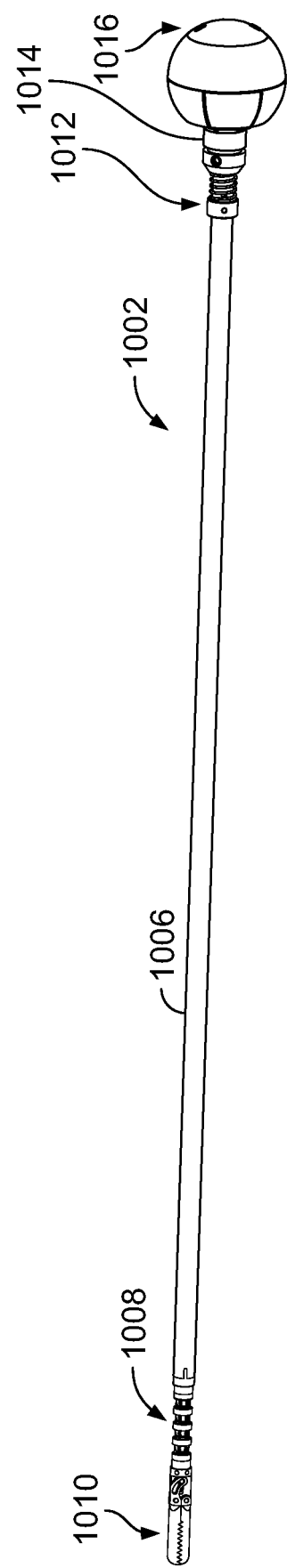
FIG. 4 is a perspective view of a shaft assembly of the laparoscopic device of FIG. 1 with the end effector in a closed configuration.

FIG. 4 illustrates a perspective view of the shaft assembly 1002 with a distal sleeve omitted to display internal features. Referring to FIG. 4, as well as FIGS. 5-7, the shaft assembly 1002 includes a shaft 1006, an articulation segment 1008 connected to a distal end of the shaft 1006, an end effector 1010 (e.g., a gripper) coupled to a distal end of the articulation segment 1008, an activation system 1012 surrounding the shaft 1006, a rotation collar 1014 surrounding a proximal end of the shaft 1006, a track ball assembly 1016 (e.g., a ball actuator) attached to the rotation collar 1014, a rod 1018 extending through the shaft 1006 to the end effector 1010, and multiple cables 1020 extending from the end effector 1010 to the track ball assembly 1016.

The shaft 1006 defines opposing slots 1056 near a proximal end of the shaft 1006 that allow translation of the rod 1018 extending therethrough. The activation system 1012 includes a collar 1052 that is translatable along the shaft 1006 and a spring 1054 that biases the collar 1052 to the position shown in FIG. 5. The rod 1018 includes a central portion 1058, a proximal pin 1060 that is attached to the collar 1052 and translatable axially within the slots 1056, a distal wire section 1064, and a distal pin 1062 that is translatable with respect to the end effector 1010 to open and close the end effector 1010, as will be discussed in more detail below with respect to FIGS. 6-10.

Figure 5:
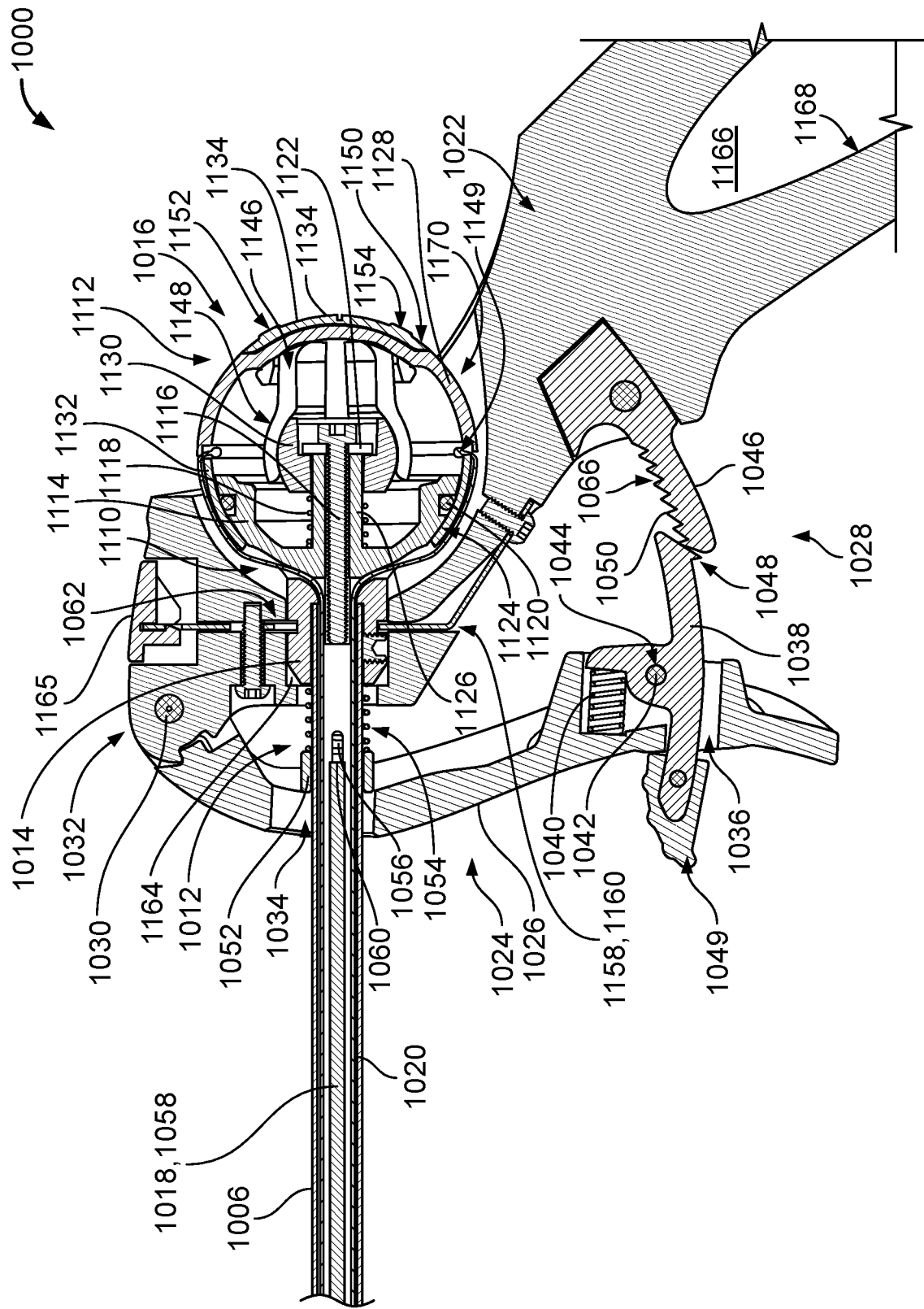
FIG. 5 is a cross-sectional view of a proximal region of the laparoscopic device of FIG. 1 corresponding to an open configuration of the end effector.

Referring to FIG. 5, the handle assembly 1004 includes a grip body 1022 for grasping the laparoscopic device 1000 and a trigger assembly 1024 for manipulating (e.g., opening, closing, locking, and releasing) the end effector 1010. The trigger assembly 1024 includes a lever 1026 and a latch mechanism 1028. The grip body 1022 is a generally elongate structure that defines a generally spherical pocket 1170 in which the track ball assembly 1016 can rotate and an opening 1166 that reduces a weight of the grip body 1022.

The lever 1026 has a curved profile and is pivotable about an axis 1030 (normal to the plane of FIG. 5) defined by a pin coupling 1032 between the lever 1026 and the grip body 1022. The lever 1026 is spring loaded by the activation system 1012 to the biased position shown in FIG. 5 and defines an opening 1034 through which the shaft 1006 passes. The lever 1026 also defines a channel 1036 to which a portion of the latch mechanism 1028 is mounted. In particular, the latch mechanism 1028 includes a ratchet finger 1038 that passes through the channel 1036, a spring 1040 by which the ratchet finger 1038 is mounted to the channel 1036 and that biases the ratchet finger 1038 to the position shown in FIG. 5, a ratchet defeat lever 1049 by which the ratchet finger 1038 can be pivoted about an axis 1042 (normal to the plane of FIG. 5) defined by a pin coupling 1044 between the ratchet finger 1038 and the lever 1026, and a ratchet rack 1046 mounted to the grip body 1022 and formed to engage the ratchet finger 1038. The ratchet finger 1038 and the ratchet rack 1046 have generally arcuate profiles. The ratchet finger 1038 includes a single tooth 1048 that can be individually indexed with (e.g., engaged by) each of multiple teeth 1050 of the ratchet rack 1046. The teeth 1050 define multiple respective valleys 1066 in which the tooth 1048 can seat.

Referring to FIGS. 5-9, the lever 1026 can be depressed (e.g., squeezed) by a user's hand (e.g., by an index or middle finger) to close the end effector 1010 and released to open the end effector 1010. When the lever 1026 is depressed, the lever 1026 pushes against the axial collar 1052 to rotate the lever 1026 about the axis 1030 inward towards the grip body 1022 such that the ratchet finger 1038 moves inward along the ratchet rack 1046. The proximal pin 1060 of the rod 1018 moves proximally with the axial collar 1052, thereby translating the distal pin 1062 of the rod 1018 proximally to close the end effector 1010, as will be discussed in more detail with respect to FIGS. 6-10.

Figure 6:
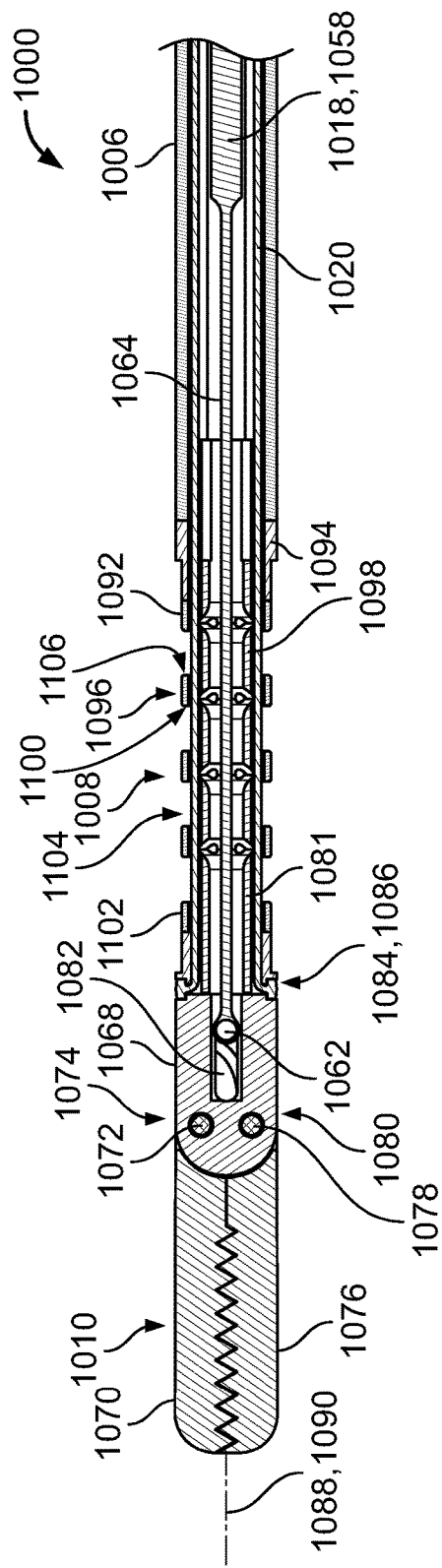
FIG. 6 is a cross-sectional view of a distal region of the laparoscopic device of FIG. 1 with the end effector in a closed configuration.
Figure 7:
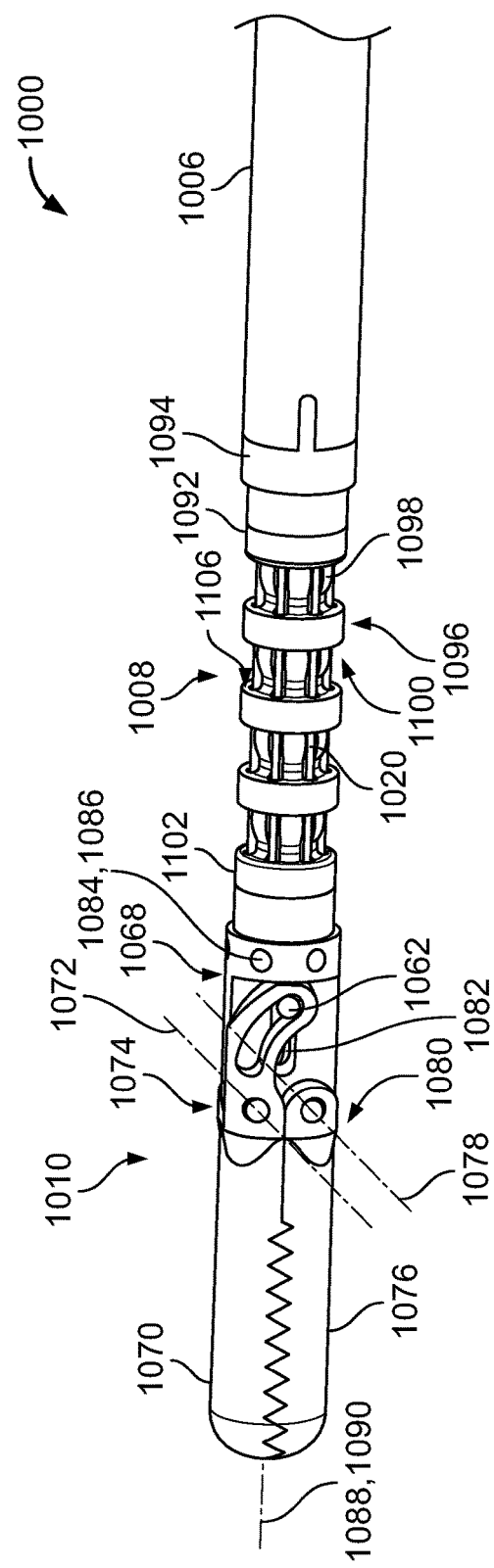
FIG. 7 is a perspective view of the distal region of FIG. 6.
Figure 9:
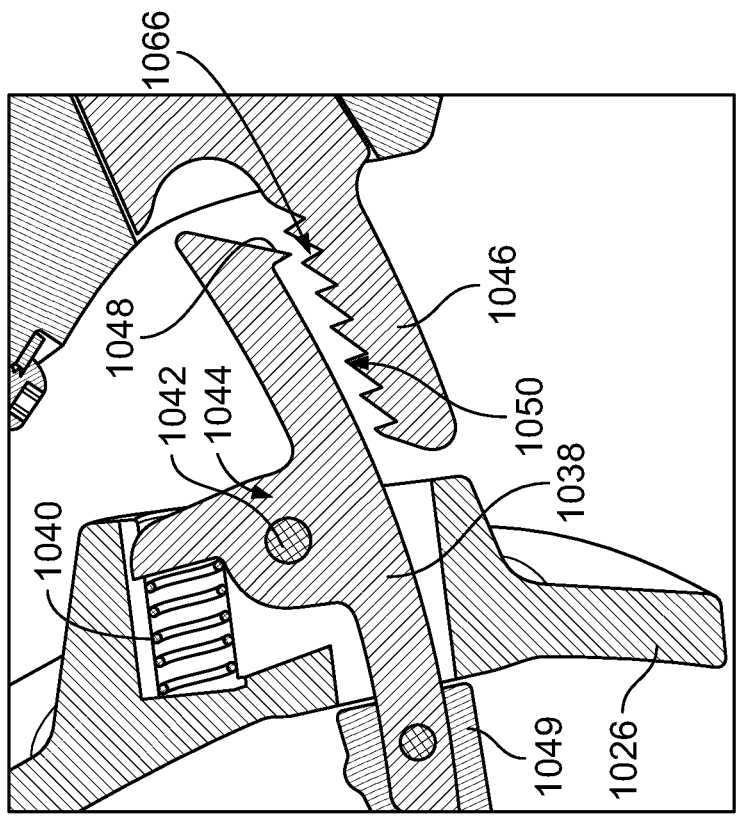
FIG. 9 is a cross-sectional view of the trigger mechanism of FIG. 8 in an unlocked configuration.
Figure 8:
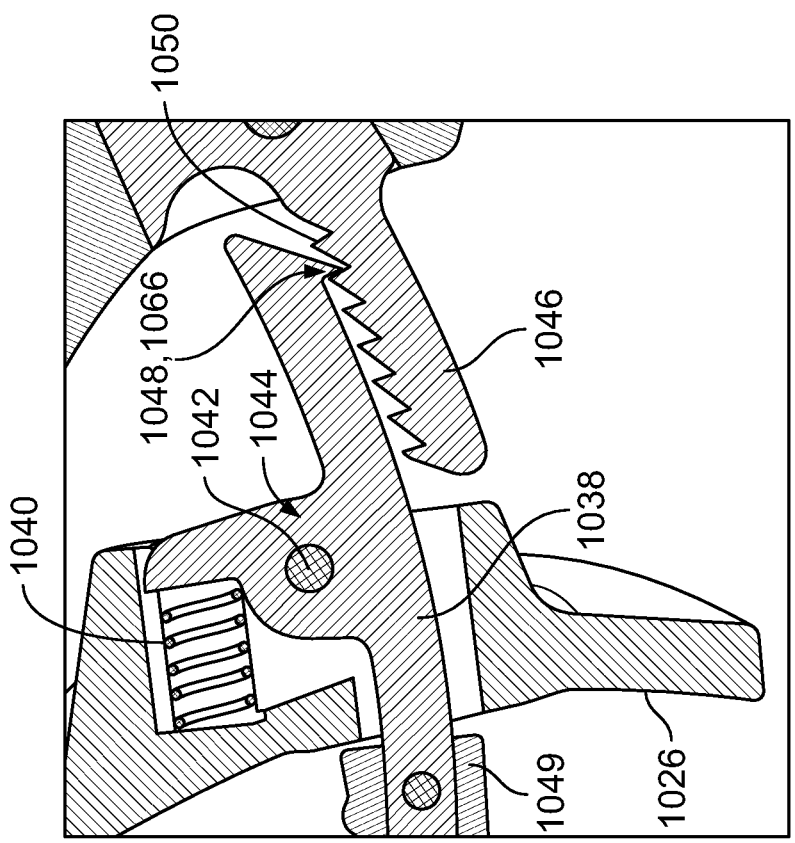
FIG. 8 is a cross-sectional view of a trigger mechanism of the laparoscopic device of FIG. 1 in a locked configuration.
Figure 10:
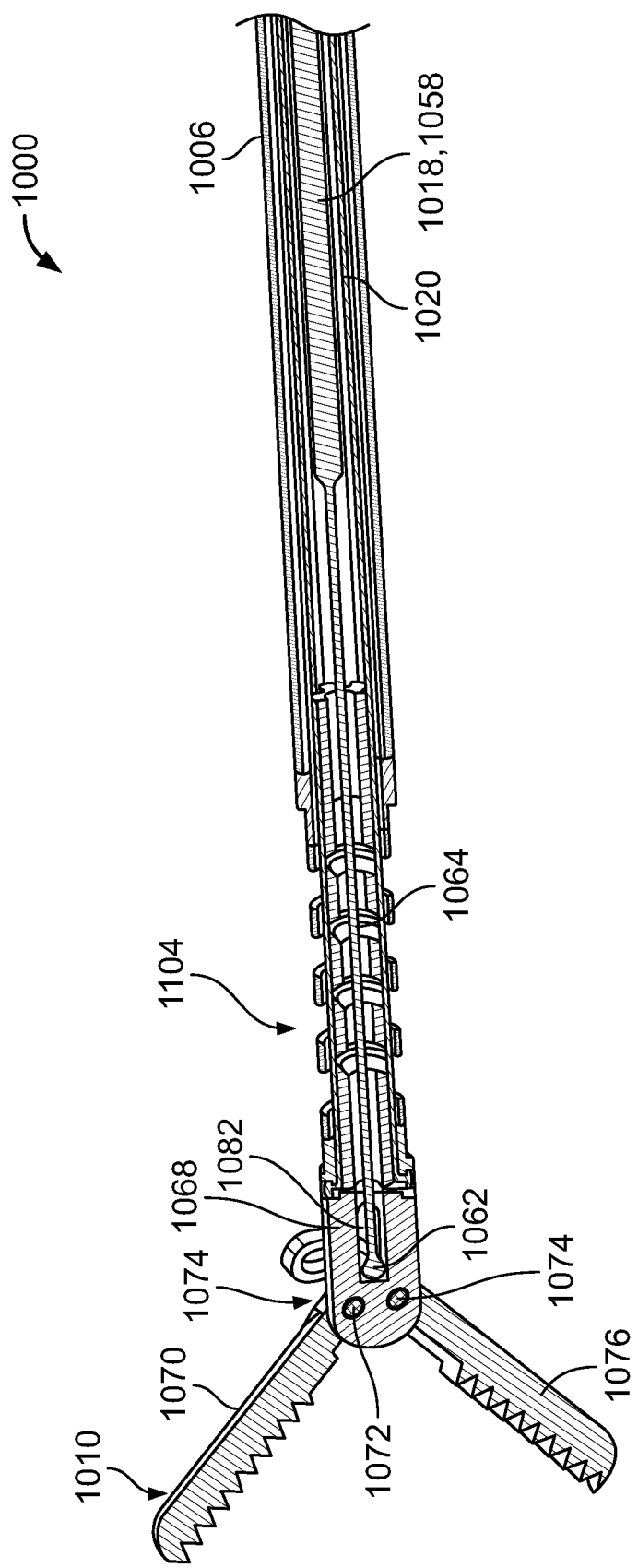
FIG. 10 is a cross-sectional view of the end effector of the laparoscopic device of FIG. 1 in an open configuration.

The latch mechanism 1028 can be locked at each valley 1066 of the ratchet rack 1046 to lock a corresponding open configuration of the end effector 1010 and can be unlocked (e.g., released or disabled) to adjust the extent to which the end effector 1010 is open. The end effector 1010 achieves a fully closed configuration (as shown in FIGS. 6 and 7) when the tooth 1048 of the ratchet finger 1036 is engaged with the inward-most tooth 1050 and valley 1066 of the ratchet rack 1046. The end effector 1010 achieves a fully open configuration (as shown in FIG. 10) when the tooth 1048 of the ratchet finger 1036 abuts the outer-most most tooth 1050 of the ratchet rack 1046 (as shown in FIG. 5). Referring to FIG. 9, the ratchet defeat lever 1049 can be depressed to pivot the ratchet finger 1038 about the axis 1042 against the spring 1040 to lift the ratchet finger 1038 up from the ratchet rack 1046 such that the ratchet finger 1038, mounted to the lever 1026, can be moved outward or inward along the ratchet rack 1046. The ratchet defeat lever 1049 can be released to allow the ratchet finger 1036 to return to the spring-loaded position and locked at a desired position along the ratchet rack 1046.

Referring to FIGS. 6 and 7, the end effector 1010 includes a support base 1068, a first jaw 1070 pivotable about an axis 1072 defined by a pin coupling 1074 between the first jaw 1070 and the support base 1068, and a second jaw 1076 pivotable about an axis 1078 defined by a pin coupling 1080 between the second jaw 1076 and the support base 1068. The support base 1068 defines a channel 1081 that is coupled to the articulation segment 1008 through which the distal wire section 1064 of the rod 1018 passes, multiple receptacles 1084 that respectively secure distal ends 1086 of the cables 1020, and a central slot 1082 along which the distal pin 1062 of the rod 1018 can translate axially to pivot the jaws 1070, 1076 respectively about the axes 1072, 1078 to open and close the end effector 1010. When the distal pin 1062 is located at a distal-most position (e.g., when the lever 1026 of the trigger assembly 1024 is fully released at the spring-loaded configuration), the jaws 1070, 1076 are fully open, as shown in FIG. 10. When the distal pin 1062 is located at a proximal-most position (e.g., when the lever 1026 of the trigger assembly 1024 is fully depressed towards the grip body 1022), the jaws 1070, 1076 are fully closed, as shown in FIGS. 6 and 7.

The articulation segment 1008 is adjustable to allow the end effector 1010 to bend in all directions. The distal wire section 1064 is a thin, compliant section (e.g., a nitinol wire) that is malleable to bend within the articulation segment 1008 such that an extent to which the end effector 1010 is open or closed is independent of an orientation of a central axis 1088 of the end effector 1010 (e.g., a central axis of the support base 1068) with respect to a central axis 1090 of the shaft 1006. The articulation segment 1008 includes a proximal socket 1092 that is coupled to a distal end portion 1094 of the shaft 1006, multiple central bearings 1096 that each include a ball 1098 and a socket 1100, and a distal ball component 1102 that is coupled to the support base 1068 of the end effector 1010. The balls 1098, 1102 respectively sit and are rotatable within the sockets 1092, 1100 to form multiple (e.g., four) ball-and-socket joints 1104 that together allow the articulation segment 1008 to bend such that the end effector 1010 can be articulated (e.g., bent) by up to about 90 degrees with respect to the central axis 1090 of the shaft 1006. The articulation segment 1008 may include a variable number of central bearings 1096 to allow the end effector 1010 to bend to varying extents.

Figure 12:
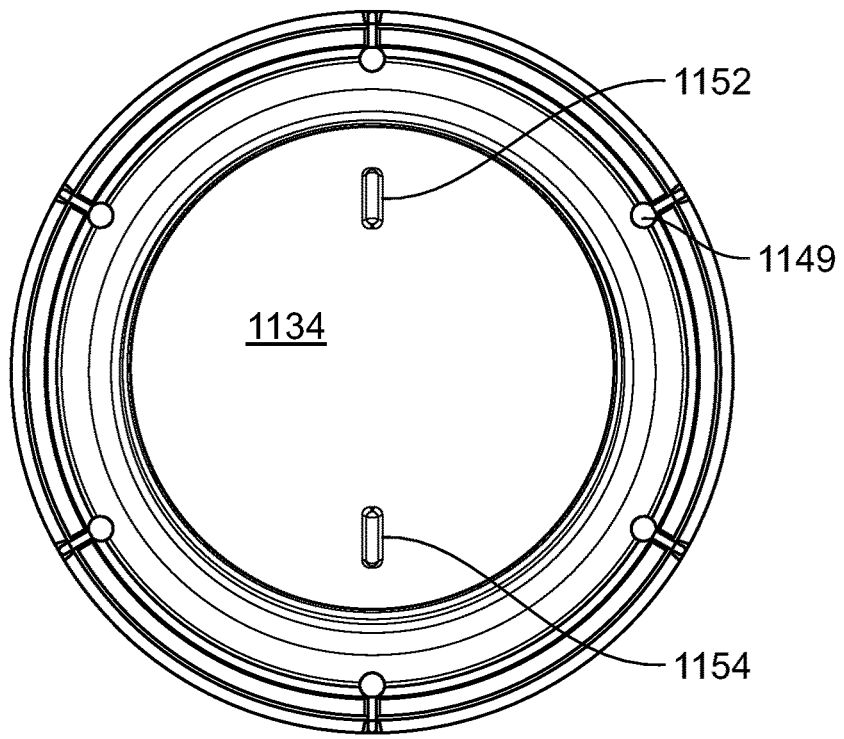
FIG. 12 is an end view of a portion of the shaft assembly of FIG. 4.
Figure 13:
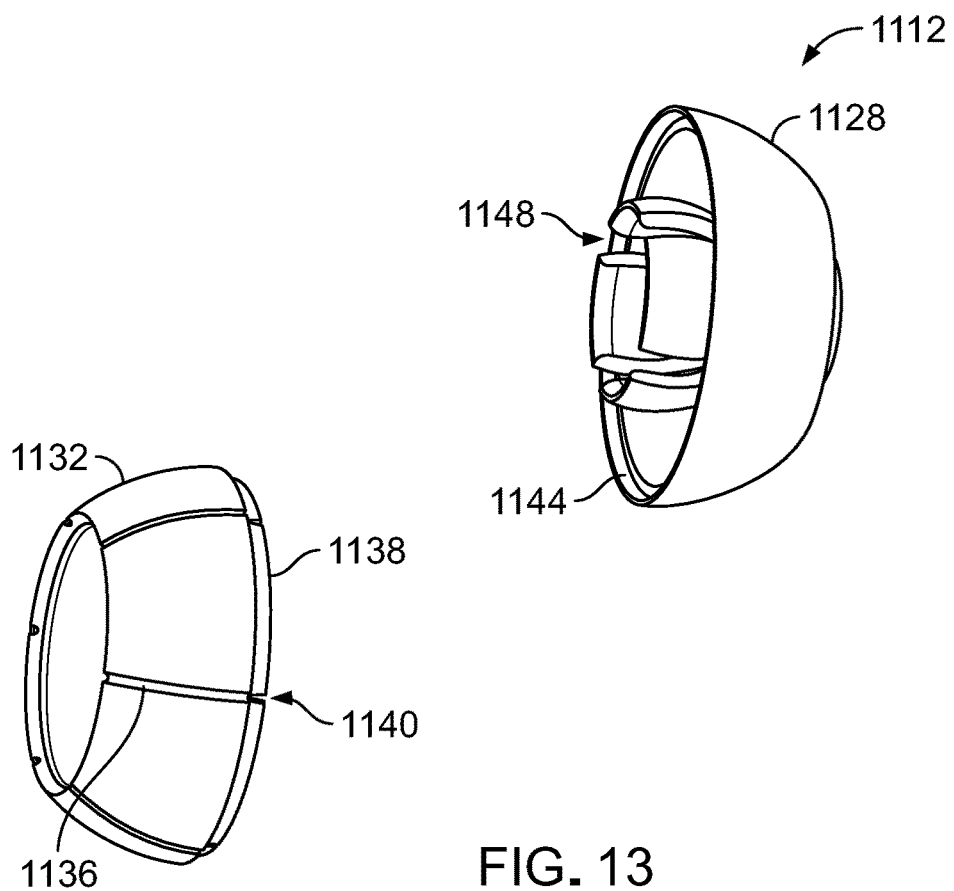
FIG. 13 is an exploded perspective view of a portion of a track ball assembly of the shaft assembly of FIG. 4.

The distal end portion 1094 of the shaft 1006, the proximal socket 1092, the central bearings 1096, and the distal ball component 1102 together define multiple (e.g., six) slots 1106 through which the cables 1020 extend proximally from the support base 1068 of the end effector 1010 into the shaft 1006. The slots 1106 are positioned along a circle that is concentric with the central axis 1090 of the shaft 1006 such that the cables 1020 are equally spaced radially from the central axis 1090 of the shaft 1006 (refer to FIG. 12). The articulation segment 1008 includes a flexible sleeve 1108 (refer to FIGS. 1-3) that surrounds and covers the proximal socket 1092, the central bearings 1096, the distal ball component 1102, and the cables 1020. The cables 1020 further extend through the shaft 1006 and proximally into the track ball assembly 1016.

Referring to FIGS. 5 and 12-15, the track ball assembly 1016 includes an inner ball assembly 1110 and an outer ball assembly 1112 that is coupled to the inner ball assembly 1110. The inner ball assembly 1110 includes an inner ball 1114, a fastener 1116 that connects the inner ball 1114 to the rotation collar 1014, a spring 1118 that biases the outer ball assembly 1112 to the position shown in FIGS. 5 and 14, an o-ring 1120 that surrounds the inner ball 1114, and an axial cap 1122 that prevents the outer ball assembly 1112 from proximally sliding off of the inner ball 1114. The inner ball 1114 is a generally spherical structure that defines an outer recess 1124 in which the o-ring 1120 sits and an inner shaft 1126 that is coupled to the outer ball assembly 1112.

The outer ball assembly 1112 includes an outer ball 1128 (e.g., a spherical housing) that is centered along the central axis 1090 of the shaft 1006, a rotation ball 1130 that is axially translatable along the inner shaft 1126, an inner ball sleeve 1132 that surrounds the inner ball 1114, and an outer ball cap 1134 that is attached to the outer ball 1128. The inner ball sleeve 1132 defines multiple slots 1136 through which the cables 1020 pass and a recessed lip 1138 defining multiple notches 1140 that secure proximal ends 1149 of the cables 1020. In the spring-loaded configuration of the spring 1118 (e.g., with the track ball assembly 1016 positioned in a non-depressed, axially released position), the inner ball sleeve 1132 is coupled snuggly to the inner ball 1114 via a friction fit with the o-ring 1120. Accordingly, the o-ring 1120 provides a brake that prevents rotation of the inner ball sleeve 1132 with respect to the central axis 1090 of the shaft 1006.

The outer ball 1128 is a generally spherical structure that defines an inner lip 1144 that seats over the recessed lip 1138 of the inner ball sleeve 1132 to further secure the proximal ends 1149 of the cables 1020. The inner lip 1144 of the outer ball 1128 and the recessed lip 1128 of the inner ball sleeve 1132 together define a circumferential channel 1156 in which the proximal ends 1149 of the cables 1020 are disposed with limited play. The outer ball 1128 further defines an inner axial sleeve 1146 that has a spherical profile 1148 (e.g., a socket) that allows the outer ball 1128 to rotate (e.g., pivot) freely around the rotation ball 1130. The outer ball 1128 also defines an outer indentation 1150 against which the outer ball cap 1134 is locked.

The outer ball cap 1134 provides an ergonomic surface by which the track ball assembly 1116 can be manipulated (e.g., depressed, released, and rotated or pivoted) to manipulate the end effector 1010. The outer ball cap 1134 defines a north cross hair 1152 and a south cross hair 1154 that indicate (e.g., correspond with) respective orientations of the first and second jaws 1070, 1076 so that a user who lacks direct vision of the end effector 1010 is aware of the orientations of the jaws 1070, 1076. The outer ball cap 1134 also provides a central, visible area 1172 between the cross hairs 1152, 1154 at which a marking can be displayed for branding the laparoscopic device 1000. In some embodiments, the outer ball cap 1134 may have a profile the projects outward from the visible area 1172 and that provides a tactile surface that can be used as a joystick to rotate the track ball assembly 1116.

In the axially released positioned of the track ball assembly 1116 (e.g., the spring-loaded position of the spring 1118), the spring 1118 applies a proximally directed breaking force to the rotation ball 1130, which carries the outer ball assembly 1112 via the inner axial sleeve 1146. In the proximal position of the outer ball assembly 1112, the inner ball 1132 seats snuggly against the o-ring 1120 such that the outer ball assembly 1112 is fixed in rotational position (e.g., unable to rotate around the rotation ball 1130 with respect to the central axis 1090 of the shaft 1006) and positions of the proximal ends 1149 of the cables 1020 are fixed. In this locked configuration of the cables 1020, the support base 1068 of the end effector 1010 is also locked, such that an articulated position (e.g., a degree of bending) of the end effector 1010 is also locked (e.g., fixed).

Figure 11:
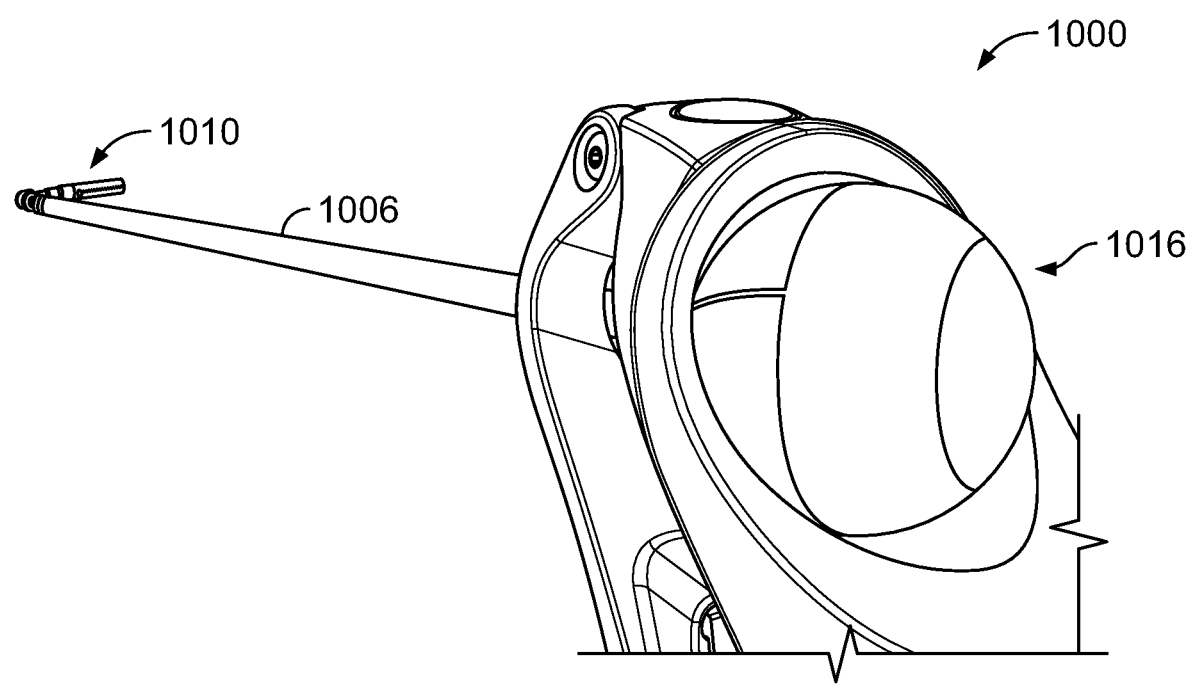
FIG. 11 is a perspective view of the laparoscopic device of FIG. 1 with the end effector in a bent configuration.
Figure 15:
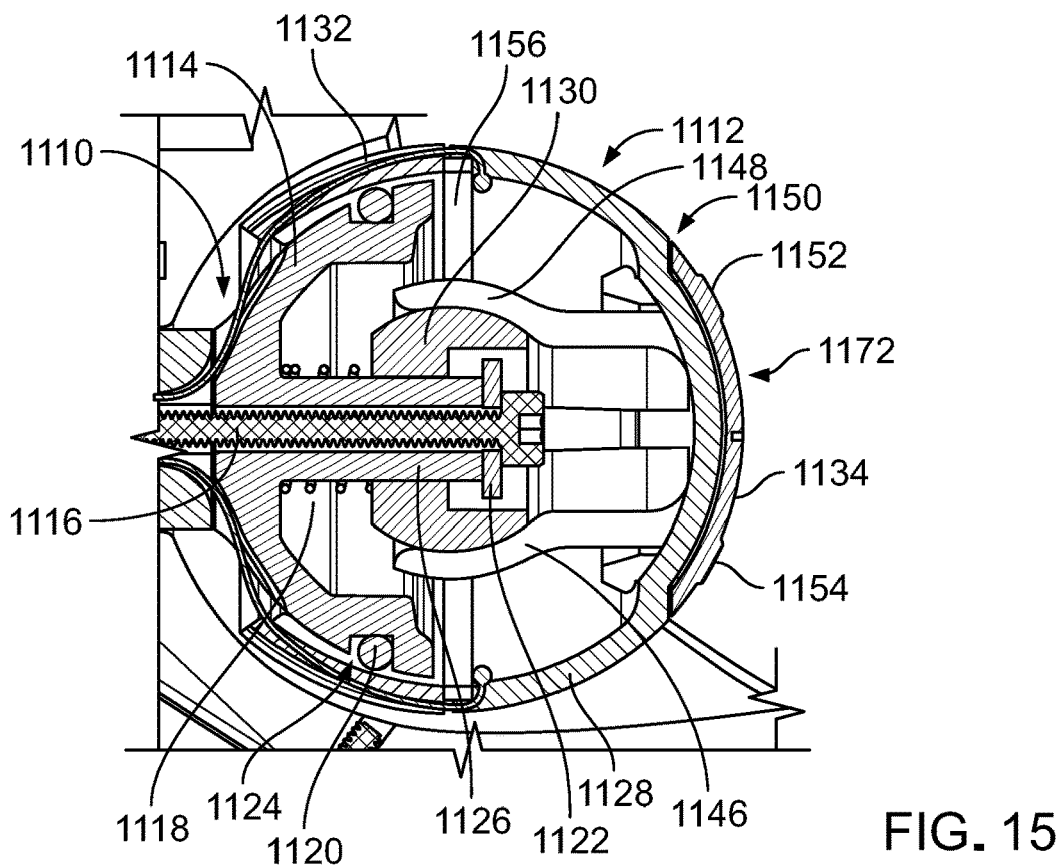
FIG. 15 is a cross-sectional view of the trackball assembly of FIG. 14 in an unlocked, released position.

The track ball assembly 1016 can be depressed (e.g., at the outer ball cap 1134) while the outer ball assembly 1112 oriented in any rotational position to unlock the articulated position of the end effector 1010. Referring to FIG. 15, when the track ball assembly 1016 is depressed, the outer ball assembly 1112 and the rotation ball 1130 are moved distally against the spring 1118 such that inner ball sleeve 1132 is pushed distally and radially apart from the inner ball 1114 and the o-ring 1120. Such distal movement of the inner ball sleeve 1132 relieves a taught configuration of the cables 1120, thereby unlocking the cables 1020. The cables 1020 are free to move, and the proximal ends 1149 of the cables 1020 are released inward of the circumferential channel 1156. In the depressed position, the outer ball 1128 (e.g., carrying the proximal ends 1149 of the cables 1020) can be pivoted freely in all directions like a thumbtack by up to about 50 degrees about the rotation ball 1130 and about any axis passing through a center point of the outer ball 1128 such that the end effector 1010 can be articulated by up to about 90 degrees. The proximal ends 1149 of the cables 1020 move with the outer ball 1128 to effect bending of the end effector 1010 via the ball-and-socket-joints 1104 and the distal ends 1086 of the cables 1020 secured to the support base 1068, as shown in FIG. 11.

Figure 14:
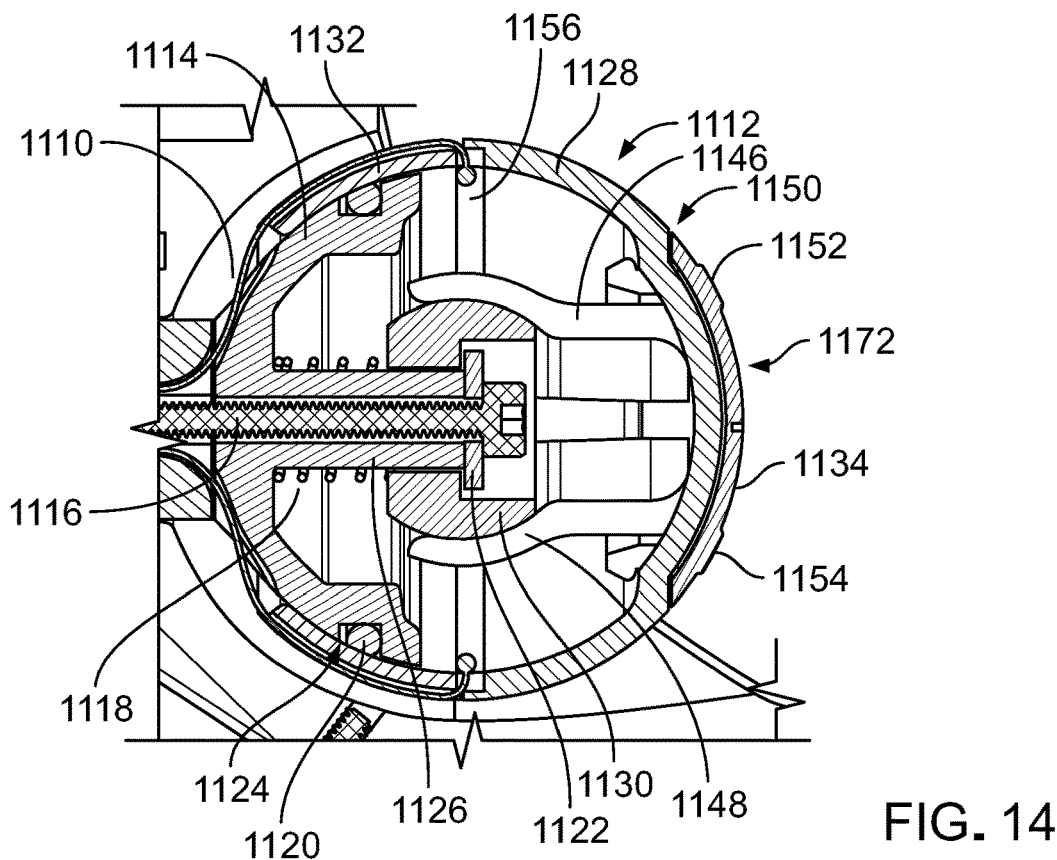
FIG. 14 is a cross-sectional view of a trackball assembly of the shaft assembly of FIG. 4 in a locked, spring-loaded position.

In the depictions shown in FIGS. 5-7, 14, and 15, the cables 1020 extend along a same side of the central axis 1090 of the shaft 1006 for an entire length of the cables 1020, such that each cable 1020 is located on same sides of the support base 1068 of the end effector 1010 and the outer ball assembly 1112. As the outer ball 1128 is rotated in a particular direction, cables 1020 disposed along a same side as the rotational direction are moved distally, such that the articulation segment 1008 and the end effector 1010 are bent in a direction opposite to that of the rotational direction. In contrast, cables 1020 disposed along the opposite side as the rotational direction are moved proximally, such that the articulation segment 1008 and the end effector 1010 are bent in the rotational direction. Cables 1020 located on opposite sides of the track ball assembly 1016 move axially by the same amount, but in opposite directions. In some embodiments, as shown in FIG. 11, the distal ends 1086 and the proximal ends 1149 of the cables 1020 may be located on opposite sides of the outer ball 1128, such that rotation of the outer ball 1128 in a particular direction causes the end effector 1010 to articulate in the same direction, in line with a "natural" articulation direction. The track ball assembly 1016 can be released from the depressed position back to the spring-loaded position (as shown in FIG. 14) to lock the articulated position of the end effector 1010. The axial cap 1122 limits an extent of proximal movement of the rotation ball 1130 (e.g., and therefore, the outer ball assembly 1112).

In the released, spring-loaded position of the track ball assembly 1016, the outer ball assembly 1112 and the inner ball assembly 1110 are fixed with respect to each other and with respect to the shaft 1006 and all components coupled thereto via the rotation collar 1014. Accordingly, the entire shaft assembly 1002 (e.g., with a fixed articulated position of the end effector 1010) can be rotated as a single unit about the central axis 1090 of the shaft 1006 by pivoting the track ball assembly 1016 left or right. The grip body 1022 of the handle assembly 1004 defines a planar slot 1158 in which a metal spring 1160 of the handle assembly 1004 is disposed. The rotation collar 1014 defines a circumferential recess 1062 in which an edge of the metal spring 1160 snap fits, allowing the rotation collar 1014, carrying all other components of the shaft assembly 1002, to rotate within a rotation receptacle 1164 as the track ball assembly 1016 is pivoted. Accordingly, the entire shaft assembly 1002 can be rotated as the track ball assembly 1016 is pivoted with a force sufficient to overcome a frictional resistance between the rotation collar 1014 and the metal spring 1160.

Figure 16:
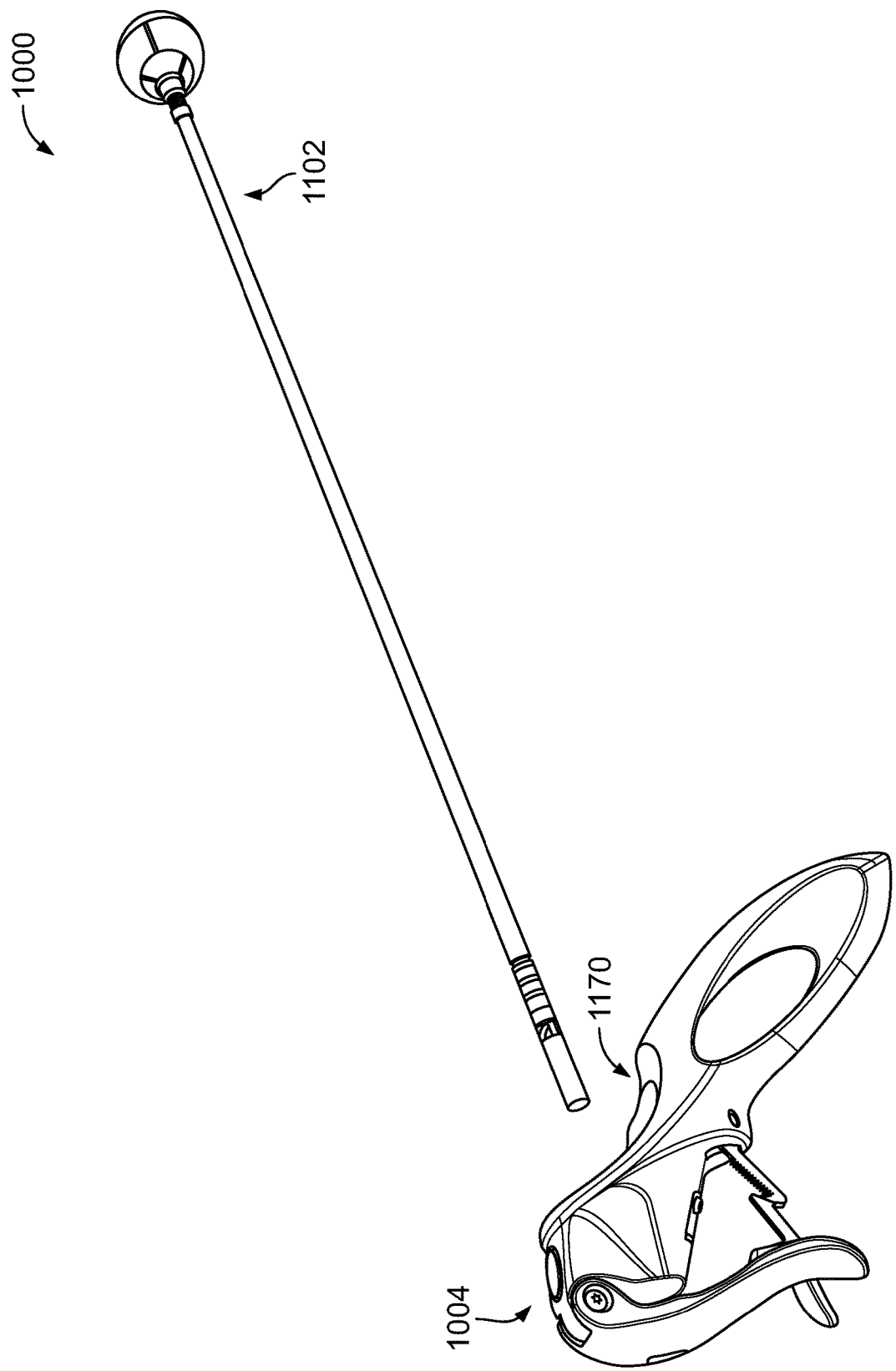
FIG. 16 is a perspective view of the laparoscopic device of FIG. 1, with the shaft assembly of FIG. 4 removed from the handle assembly.

Referring to FIGS. 5 and 16, the entire shaft assembly 1002 (e.g., as a single unit) can also be separated from the handle assembly 1004. The handle assembly 1004 includes a release button 1165 that is attached to the metal spring 1160. The shaft assembly 1002 can be released from the handle assembly 1004 by depressing the release button 1165 to lower the metal spring 1160, thereby disengaging the metal spring 1160 from the rotation collar 1014. The shaft assembly 1002 can then be removed (e.g., pulled proximally) from the handle assembly 1004. In this regard, the handle assembly 1004 can be disinfected and re-used with another shaft assembly. The shaft assembly 1002 can be assembled with the handle assembly 1004 by inserting the shaft 1006 distally into the rotation receptacle 1164 until the inner edge of the metal spring 1160 snaps into the circumferential ring 1162 of the rotation collar 1014, which secures the shaft assembly 1002 to the handle assembly 1004.

The laparoscopic device 1000 is an ergonomic, easy-to-use, and intuitive tool that provides multiple functions. Such functions include opening and closing of the end effector 1010, locking and unlocking (e.g., releasing) of an open/closed configuration of the end effector 1010, articulation (e.g., bending) of the end effector 1010, locking and unlocking of an articulated configuration of the end effector 1010, rotation of the shaft assembly 1002, and removal and installation of the shaft assembly 1002. Furthermore, the laparoscopic device 1000 can exhibit more than one configuration respectively associated with these functions at the same time due to couplings among the component parts of the laparoscopic device, even while the functions can be executed independently of one another. For example, while the laparoscopic device 1000 can exhibit a "roticulated" configuration in which both the end effector 1010 is articulated (e.g., whether bent or in-line) with respect to the central axis 1090 of the shaft 1006 and in which the shaft assembly 1002 is rotated with respect to a nominal orientation, articulation of the end effector 1010 and rotation of the shaft assembly 1002 can be carried out independently of each other. Additionally, the jaws 1076, 1076 may be open or closed in any articulated position of the end effector 1010 and in any rotational position of the shaft assembly 1002.

Accordingly, a user can manipulate the laparoscopic device 1000 to perform one or more of these functions to carry out a laparoscopic procedure. For example, in some examples, a user's thumb is used to manipulate the trackball assembly 1016. In some examples, a user's middle finger and/or index finger is used to manipulate the trigger assembly 1024. In some examples, a user's ring and pinky fingers may rest on or grip a lower portion of the handle assembly 1004. In some examples, a user's index finger may float atop the laparoscopic device 1000.

In some embodiments, the shaft assembly 1002 is a disposable device that may be discarded after a single use.

In some embodiments, the shaft assembly 1002 is a reusable device that may be disinfected between each of multiple uses. The shaft 1006 typically has a length of about 30 cm to about 40 cm (e.g., about 30 cm) and an outer diameter of about 4 mm to about 10 mm (e.g., about 5 mm) such that the shaft 1006 can pass through trocars of standard sizes. The shaft 1006 is typically made of one or more materials, such as stainless steel. The cables 1020 are typically made of one or more compliant materials, such as stainless steel. The cables 1020 can withstand a tension of up to about 15 N to about 30 N. The cables 1020 typically have a total length of about 36 cm to about 40 cm (e.g., about 36 cm). The outer ball assembly 1112 typically has a diameter of about 2.0 cm to about 5.0 cm (e.g., about 2.8 cm). Such a large diameter provides an improved manipulation of the track ball assembly 1016, since an extent of articulation of the end effector 1010 is proportional to a radius of the track ball assembly 1016. The proximal socket 1092, the central bearings 1096, and the distal ball component 1102, together forming the ball-and-socket joints 1104, are precision molded from one or more chemically resistant, corrosion resistant plastic or metal materials, such as acrylonitrile butadiene styrene (ABS), polycarbonate, polyvinyl chloride (PVC), polyoxymethylene (POM), aluminum, titanium, or polyetherimide (PEI). The grip body 1022 of the handle assembly 1004 is typically made of one more materials, such as stainless steel or any of the materials from which the ball-and-socket joints are formed.

Figure 17:
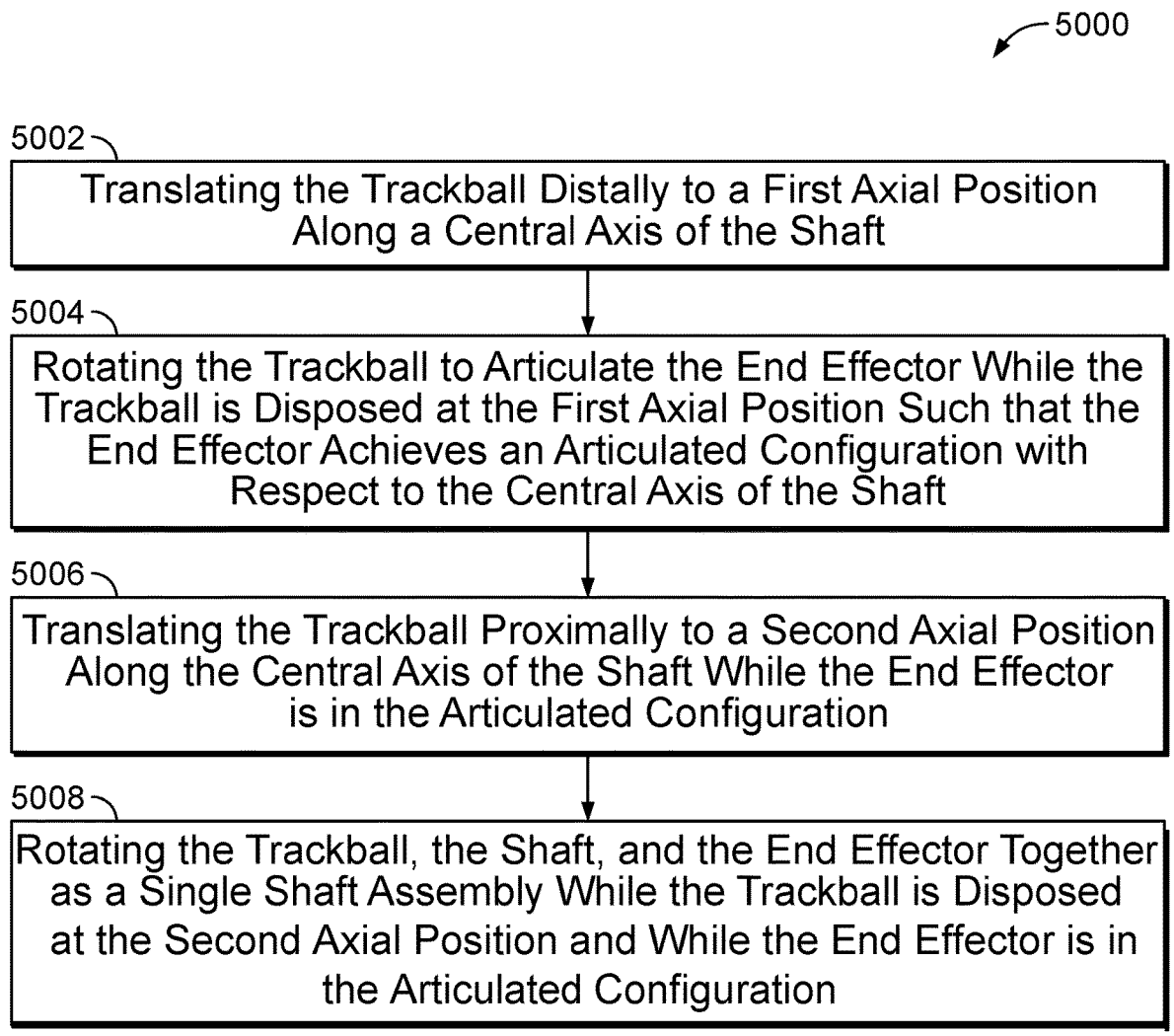
FIG. 17 is a flowchart illustrating a method of using the laparoscopic device of FIG. 1.

FIG. 17 illustrates an example process 5000 for using the laparoscopic device 1000 to perform a laparoscopic procedure. In some implementations, the process includes translating a trackball (e.g., the outer ball assembly 1112) distally to a first axial position (e.g., the released position, shown in FIG. 15) along a central axis (e.g., the central axis 1090) of a shaft (e.g., the shaft 1006) (5002). In some implementations, the process further includes rotating the trackball to articulate an end effector (e.g., the end effector 1010) while the trackball is disposed at the first axial position such that the end effector achieves an articulated configuration (e.g., as shown in FIG. 11) with respect to the central axis of the shaft (5004). In some implementations, the process further includes translating the trackball proximally to a second axial position (e.g., the locked, spring-loaded position, shown in FIG. 14) along the central axis of the shaft while the end effector is in the articulated configuration (5006). In some implementations, the process further includes rotating the trackball, the shaft, and the end effector together as a single shaft assembly (e.g., the shaft assembly 1002) while the trackball is disposed at the second axial position and while the end effector is in the articulated configuration (5008).

A number of embodiments and implementations have been described above. However, it will be understood that various modifications may be made without departing from the spirit and scope of the disclosure. For example, while the laparoscopic device 1000 has been described and illustrated as including a set of jaws as an end effector, in some embodiments, a laparoscopic device that is otherwise similar to the laparoscopic device 1000 may include the handle assembly 1004 and a shaft assembly that has a different type of end effector, such as various types of graspers, forceps, dissectors, needle holders, suture capture devices, scissors, biopsy punches, and electrosurgical devices.

While the laparoscopic device 1000 has been described and illustrated as including a pistol grip type handle assembly 1004, in some embodiments, a laparoscopic device that is otherwise similar to the laparoscopic device 1000 may include the handle assembly 1004 of a different type, such as a reverse pistol grip, a pencil grip, a tweezer grip, a scissors/forceps grip, a riffle grip, or a dagger grip. Furthermore, owing to the modular (e.g., separable) nature of the shaft assembly and the handle assembly, several different laparoscopic device configurations can be achieved by selecting a particular combination of a desired shaft assembly and a desired handle assembly.

While the components of the laparoscopic device 1000 have been described and illustrated as having certain dimensions, sizes, and shapes, in some embodiments, a laparoscopic device that is otherwise similar to the laparoscopic device 1000 may include like components that have different dimensions, sizes, and/or shapes.

While the laparoscopic device 1000 has been described and illustrated as including six cables 1020 and four ball-and-socket joints 1104, in some embodiments, a laparoscopic device that is otherwise substantially similar in construction and function to the laparoscopic device 1000 may include a different number of cables 1020 and/or a different number of ball-and-socket joints 1104 and associated features.

Figure 18:
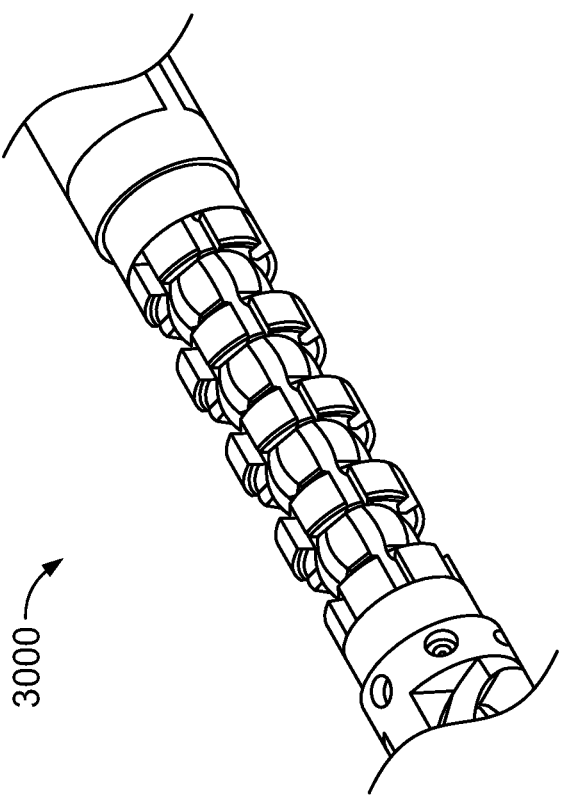
FIG. 18 is a perspective view of an articulation segment of a laparoscopic device.

While the proximal socket 1092, the central bearings 1096, and the distal ball component 1102 have been described and illustrated as including internal slots 1106 through which the cables 1020 pass, in some embodiments, a laparoscopic device 3000 that is otherwise substantially similar in construction and function to the laparoscopic device 1000 may include ball and socket components that define open cable slots in which cables are held in by a surrounding sleeve (not shown), as shown in FIG. 18.

Figure 19:
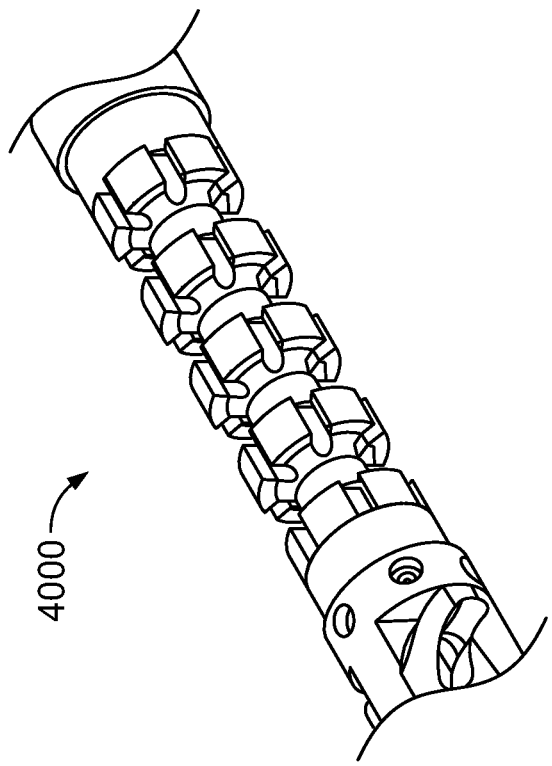
FIG. 19 is a perspective view of an articulation segment of a laparoscopic device.

While the proximal socket 1092, the central bearings 1096, and the distal ball component 1102 have been described and illustrated as separate components, in some embodiments, a laparoscopic device 4000 that is otherwise substantially similar in construction and function to the laparoscopic device 1000 may include ball-and-socket joints that are defined by a single molded, bendable component, as shown in FIG. 19.

While the example process 5000 of using the laparoscopic device 1000 has been described with a certain order of certain operations, in some implementations, similar methods of using the laparoscopic device 1000 can include operations that are reverse to those described in the process 5000 or can include the same or different operations performed in a different order.

Figure 22:
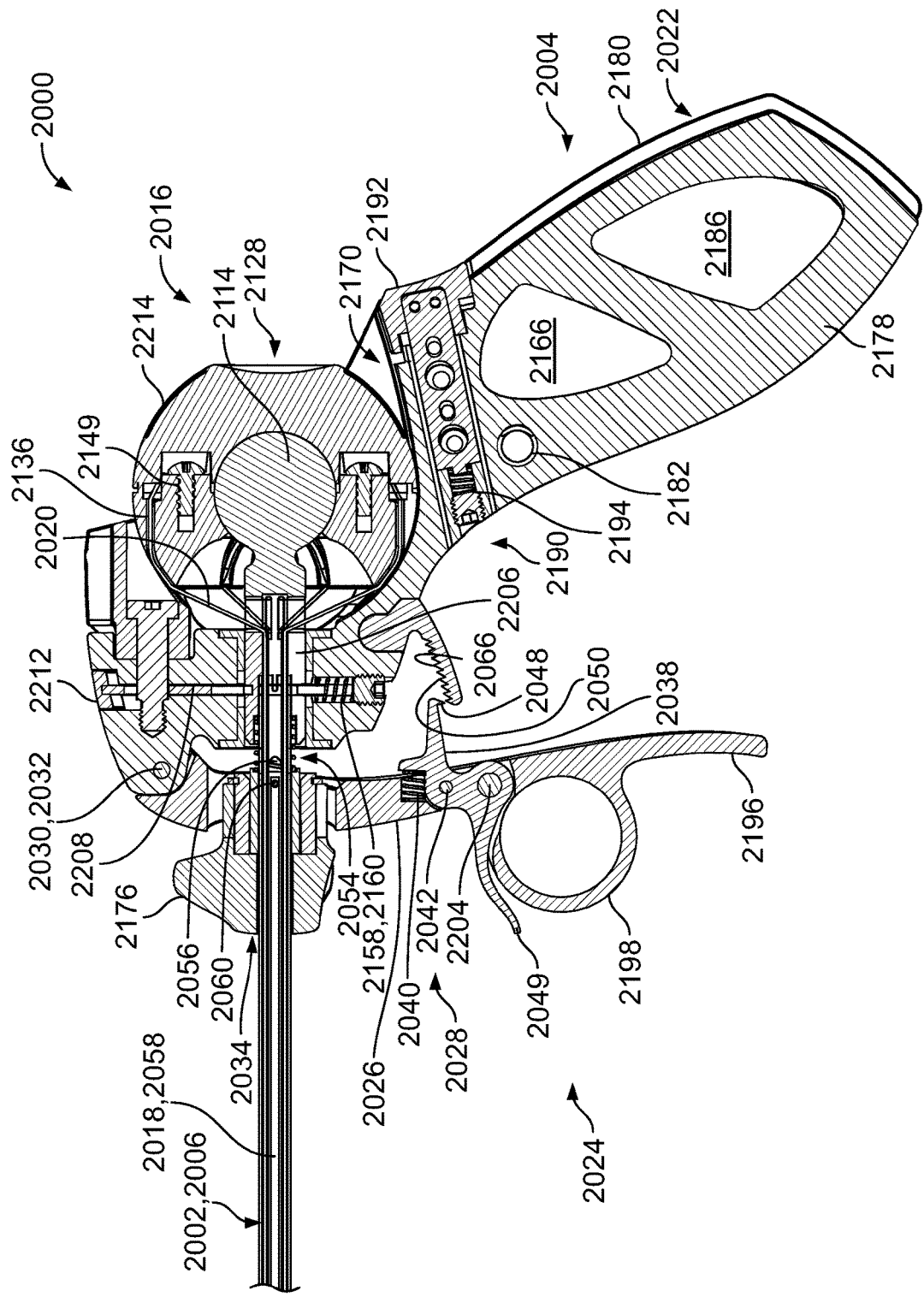
FIG. 22 a cross-sectional view of a proximal region of the laparoscopic device of FIG. 20 corresponding to an open configuration of the end effector.

Other embodiments of a laparoscopic device are also possible. For example FIGS. 20-22 illustrate a laparoscopic device 2000 designed for performing laparoscopic surgical procedures within a body cavity (e.g., an abdominal cavity) of a patient. The laparoscopic device 2000 includes a shaft assembly 2002 that is constructed to manipulate tissues within the body cavity and a handle assembly 2004 that is coupled to the shaft assembly 2002 for manipulating the shaft assembly 2002. The shaft assembly 2002 is separable from the handle assembly 2004 (refer to FIG. 24) and is rotatable with respect to the handle assembly 2004.

The shaft assembly 2002 includes a shaft 2006, an articulation segment 2008 connected to a distal end of the shaft 2006, an end effector 2010 (e.g., a gripper) coupled to a distal end of the articulation segment 2008, a track ball assembly 2016 (e.g., a ball actuator) attached to a proximal end of the shaft 2006, a spinner 2176 coupled to the shaft 2006 at a location distal to the track ball assembly 2016, a rod 2018 extending through the shaft 2006 to the end effector 2010, and multiple cables 2020 extending from the end effector 2010 to the track ball assembly 2016. The spinner 2176 can be spun (e.g., rotated) by a user to rotate the entire shaft assembly 2002 with respect to the handle assembly 2004.

The shaft 2006 defines opposing slots 2056 near a proximal end of the shaft 2006 that allow translation of the rod 2018 extending therethrough. The rod 2018 includes a central portion 2058, a proximal pin 2060 that is translatable axially within the slots 2056, and a distal wire section 2064 that is translatable and coupled to the end effector 2010 to open and close the end effector 2010, as will be discussed in more detail below.

Referring to FIGS. 22, 23, 29, and 30, the handle assembly 2004 includes a grip body 2022 for grasping the laparoscopic device 2000 and a trigger assembly 2024 for manipulating (e.g., opening, closing, locking, and releasing) the end effector 2010. The grip body 2022 includes a central portion 2178 (e.g., a central handle member) by which the track ball assembly 2016 can be attached to and detached from the shaft assembly 2002. The grip body 2022 also includes two outer portions 2180, 2200 (e.g., first and second gripping members) by which a bent configuration of the articulation segment 2008 can be locked and by which a rotational position of the shaft assembly 2002 can be locked. The outer portions 2180, 2200 flank the central portion 2178 and can be squeezed together (e.g., inwards towards the central portion 2178) from the biased position shown in FIG. 30 to compress an outer ball 2128 (e.g., a rounded housing) of the track ball assembly 2016 to lock a rotational position of the track ball assembly 2016. The shaft assembly 2002 can withstand a force of about 15 N to about 20 N to resist rotational movement or lateral movement while the grip body 2022 is in the compressed configuration.

Figure 23:
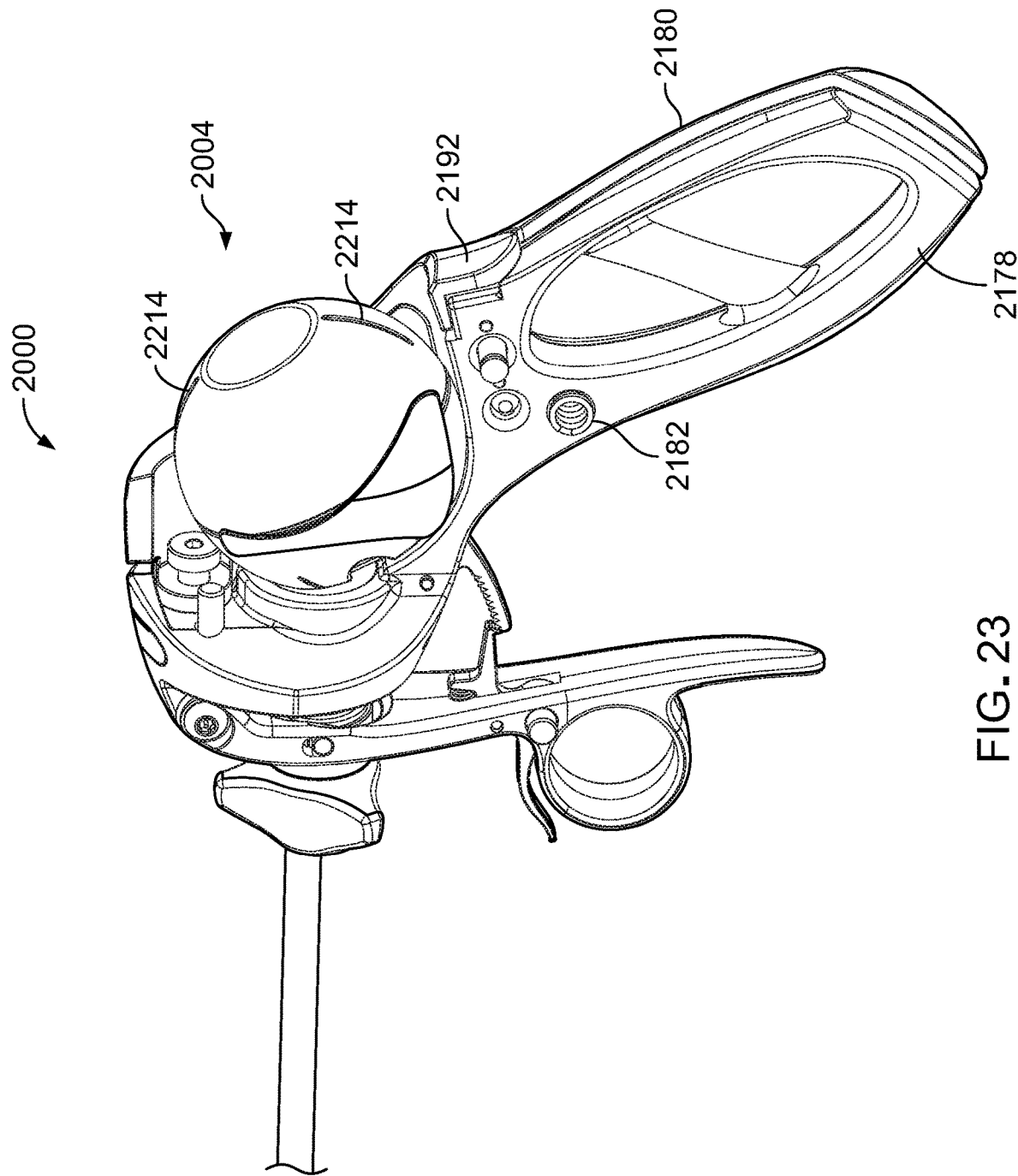
FIG. 23 is a perspective view of the proximal region of the laparoscopic device of FIG. 20, with certain outer components omitted to illustrate certain internal components.

Compression of the outer ball 2128 with the outer portions 2180, 2200 also locks a bent configuration of the articulation segment 2008, due to fixed attachments of proximal ends 2149 of the cables 2020 to the outer ball 2128. Referring to FIG. 23, the central portion 2178 carries a spring 2182 that biases the outer portions 2180, 2200 to an expanded configuration in which lower end regions of the outer portions 2180, 2200 are spaced apart from central portion 2178. In the expanded configuration, a sufficient clearance 2184 is present between the outer ball 2128 and the outer portions 2180, 2200 of the grip body 2022 (refer to FIG. 30) to allow rotation of the outer ball 2128, and therefore rotation of the entire track ball assembly 2016 with respect to the handle assembly 2004. The central portion 2178 and the outer portions 2180, 2200 together define a round pocket 2170 in which the track ball assembly 2016 can rotate and two openings 2166, 2186 that reduce a weight of the grip body 2022 (refer to FIG. 22). Sufficient squeezing of the two outer portions 2180, 2200 together locks the outer portions 2180, 2200 to the central portion 2178 via coupling of the outer portions 2180, 2200 to a pin 2188 carried by the central portion 2178. The outer ball 2128 defines multiple ridges 2214 that improve tactile grip of the outer ball 2128 for pivoting and rotating.

Referring to FIGS. 22 and 23, the central portion 2178 also carries a lock release mechanism 2190 that can be depressed to release the locked (e.g., compressed) configuration of the grip body 2022 to permit rotation and articulation of the shaft assembly 2002. The lock release mechanism 2190 accordingly includes a button 2192 that can be depressed, as well as a spring 2194 that biases the button 2192 to the extended configuration shown in FIG. 22 and that permits distal movement of the lock release mechanism 2190 when the button 2192 is depressed.

The trigger assembly 2024 includes a lever 2026 and a latch mechanism 2028. The lever 1026 has a curved profile and is pivotable about an axis 2030 (normal to the plane of FIG. 22) defined by a pin coupling 2032 between the lever 2026 and the central portion 2178 of the grip body 2022. The lever 2026 is spring loaded by the spring 2054 to the biased position shown in FIG. 22 and defines an opening 2034 through which the shaft 2006 passes. The lever 2026 includes a pull 2196 and a ring grip 2198 in which a user can insert his or her finger to move the lever 2026.

The latch mechanism 2028 includes a ratchet finger 2038, a spring 2040 by which the ratchet finger 2038 is mounted to the lever 2026 and that biases the ratchet finger 2038 to the position shown in FIG. 22, a ratchet defeat lever 2049 by which the ratchet finger 2038 can be pivoted about a pin 2042 (normal to the plane of FIG. 22) carried by the lever 2026. In this manner, the ratchet defeat leaver 2049 provides an on-demand, "live" ratchet defeat mechanism. The latch mechanism 2028 further includes a ratchet rack 2046 mounted to the central portion 2178 of the grip body 1022 and formed to engage the ratchet finger 2038. The ratchet finger 2038 and the ratchet rack 2046 have generally arcuate profiles. The ratchet finger 2038 includes a single tooth 2048 that can be individually indexed with (e.g., engaged by) each of multiple teeth 2050 of the ratchet rack 2046. The teeth 2050 define multiple respective valleys 2066 in which the tooth 2048 can seat. The latch mechanism 2028 also includes an actuator 2204 by which the ratchet defeat mechanism can be locked (e.g., providing a fixed ratchet defeat) in a configuration (shown in FIGS. 20-22) that allows free movement of the tooth 2048 along the ratchet rack 2046. such that the ratchet defeat lever 2049 does not need to be used on-demand.

Figure 26:
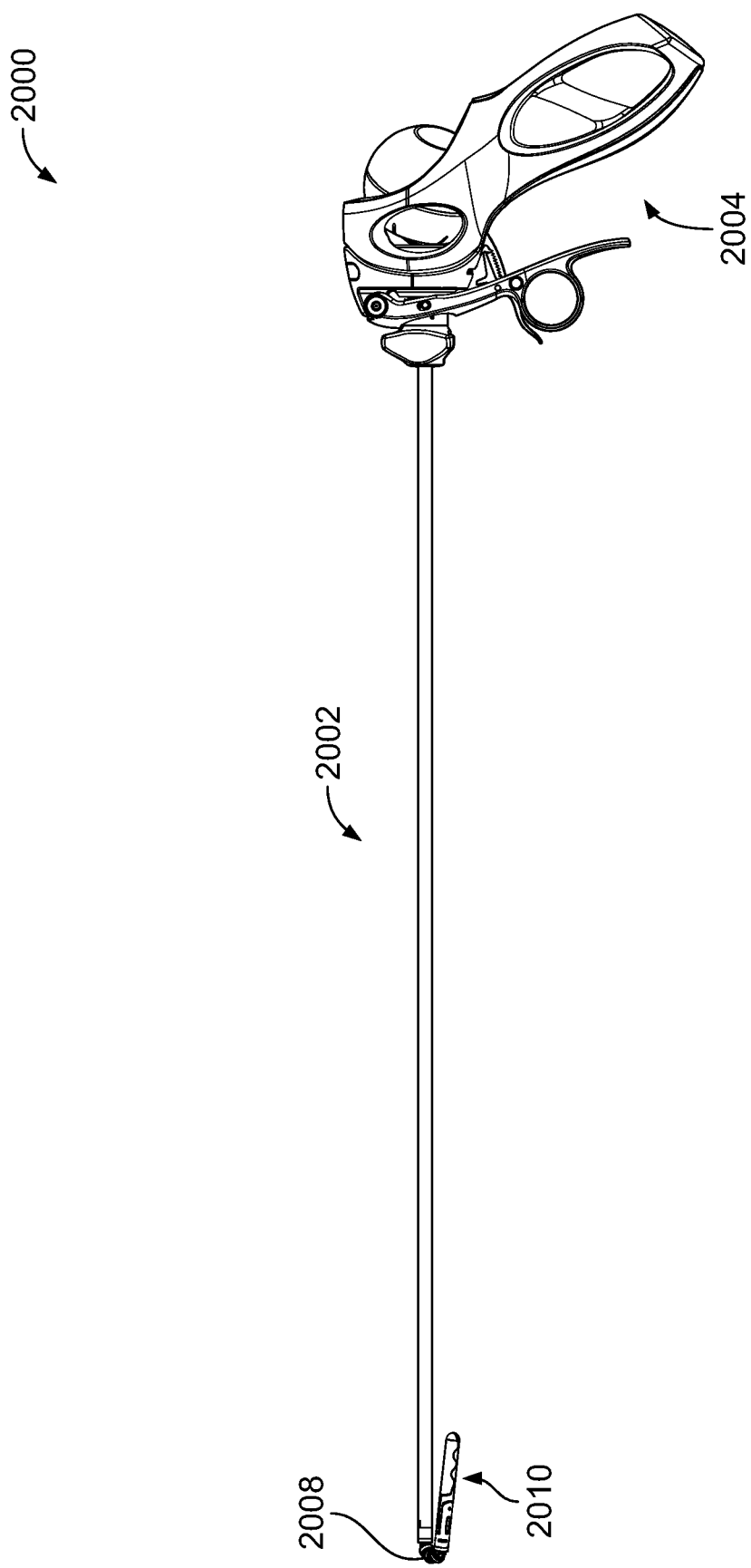
FIG. 26 is a side view of the laparoscopic device of FIG. 20, with the end effector in a closed and bent configuration.
Figure 28:
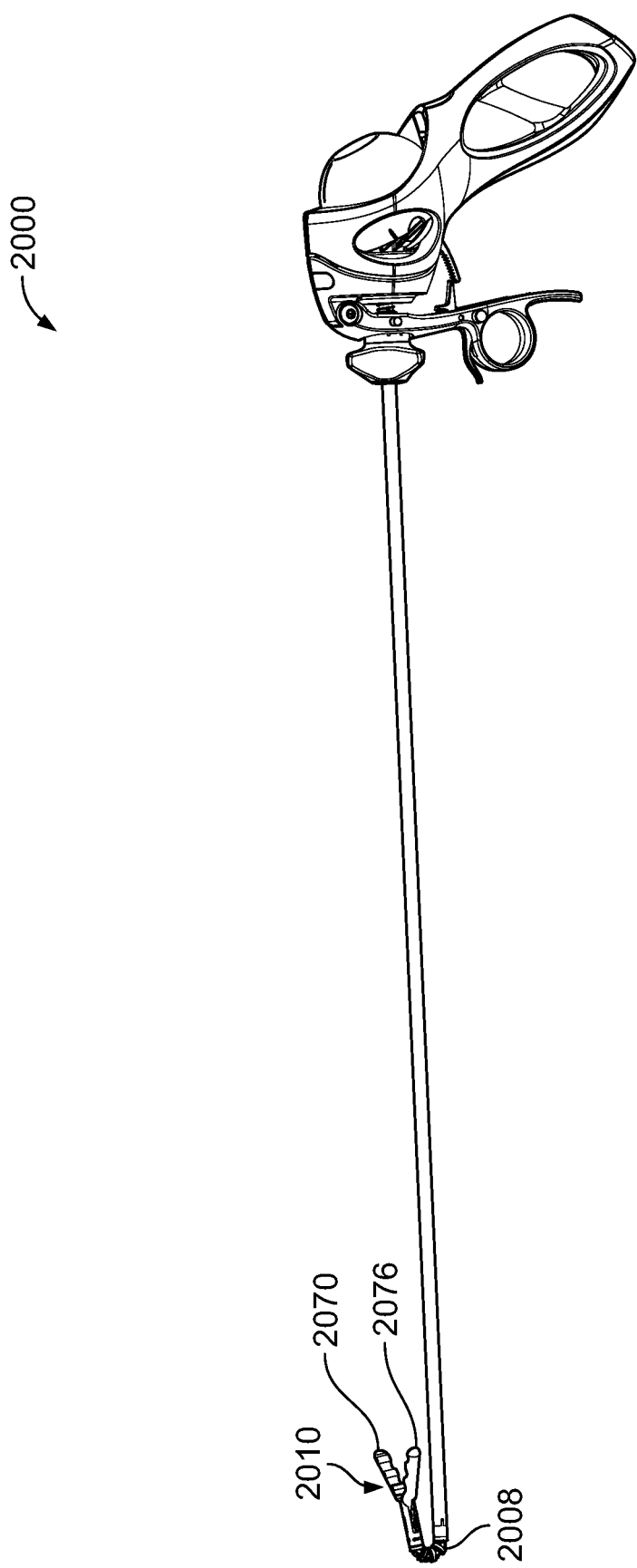
FIG. 28 is a perspective view of the laparoscopic device of FIG. 20, with the end effector in an open and bent configuration.
Figure 29:
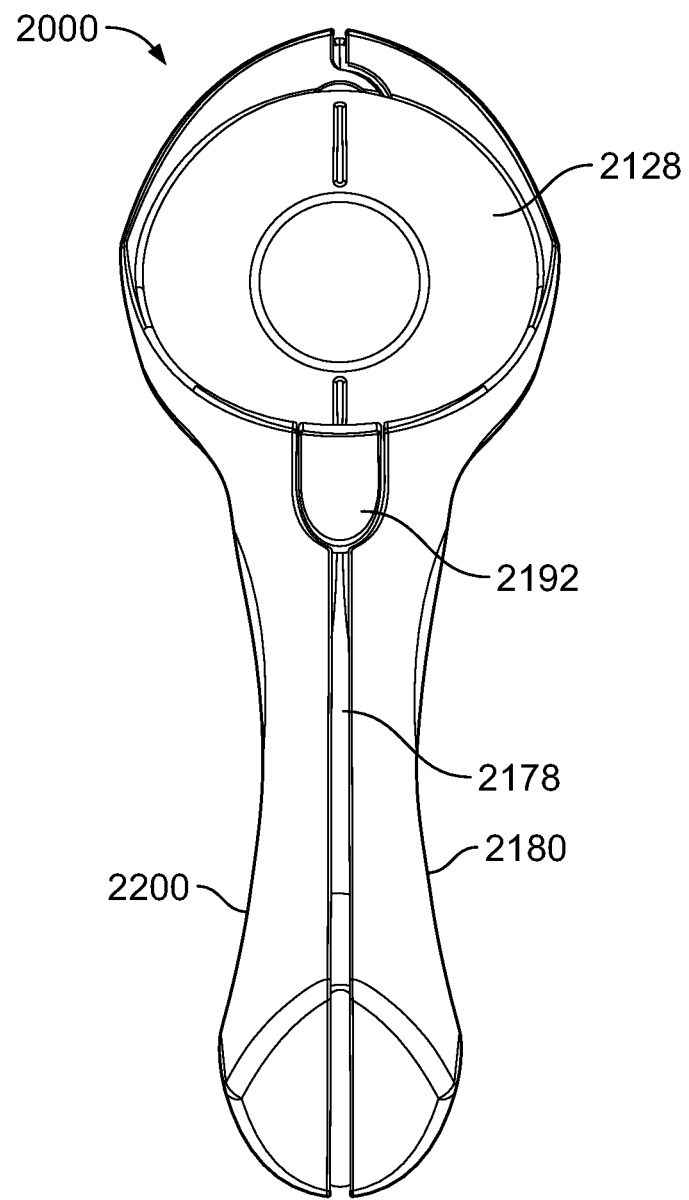
FIG. 29 is a rear view of the laparoscopic device of FIG. 20 including a handle in a compressed configuration.
Figure 30:
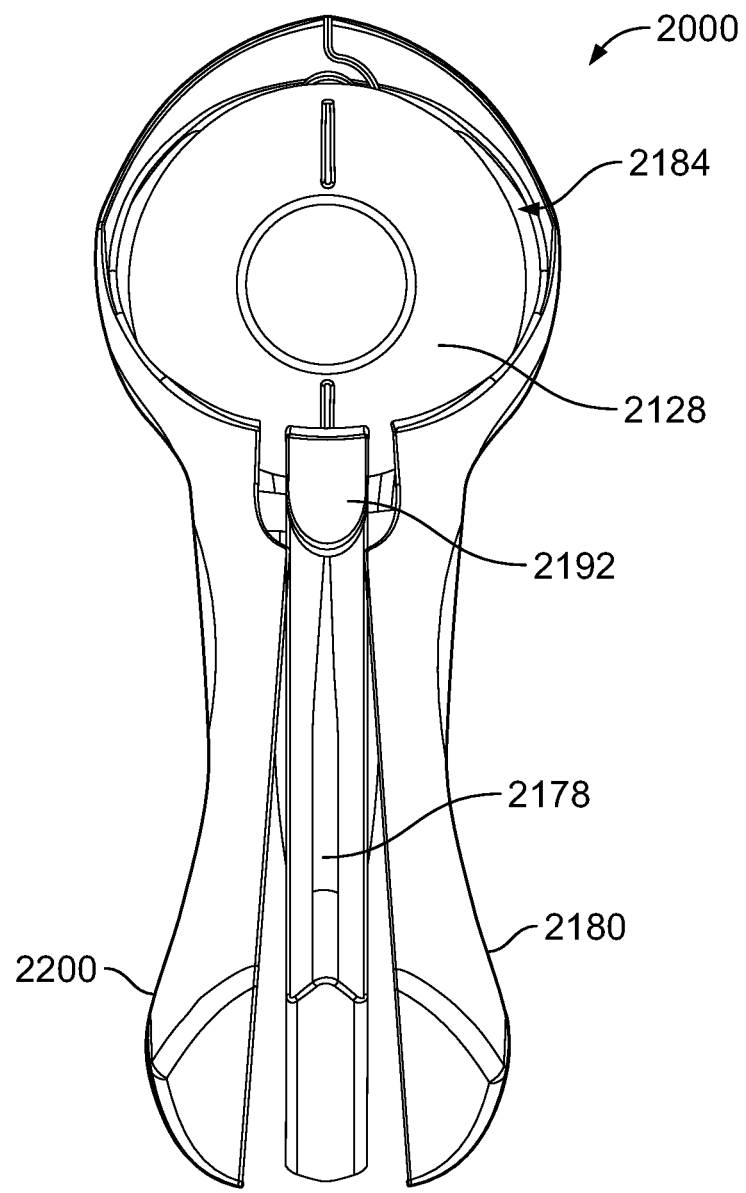
FIG. 30 is a rear view of the laparoscopic device of FIG. 20 including the handle in an expanded configuration.

Referring respectively to FIGS. 26 and 28, the lever 2026 can be depressed (e.g., squeezed) by a user's hand (e.g., by an index or middle finger) to close the end effector 2010 and released to open the end effector 2010. When the lever 2026 is depressed (e.g., while the ratchet defeat is free), the ratchet finger 2038 moves inward along the ratchet rack 2046. The proximal pin 2060 of the rod 2018 moves proximally, thereby translating the distal wire section 2064 (e.g., having an interior position indicated schematically by a dashed line in FIG. 32) of the rod 2018 proximally to close the end effector 2010.

Figure 27:
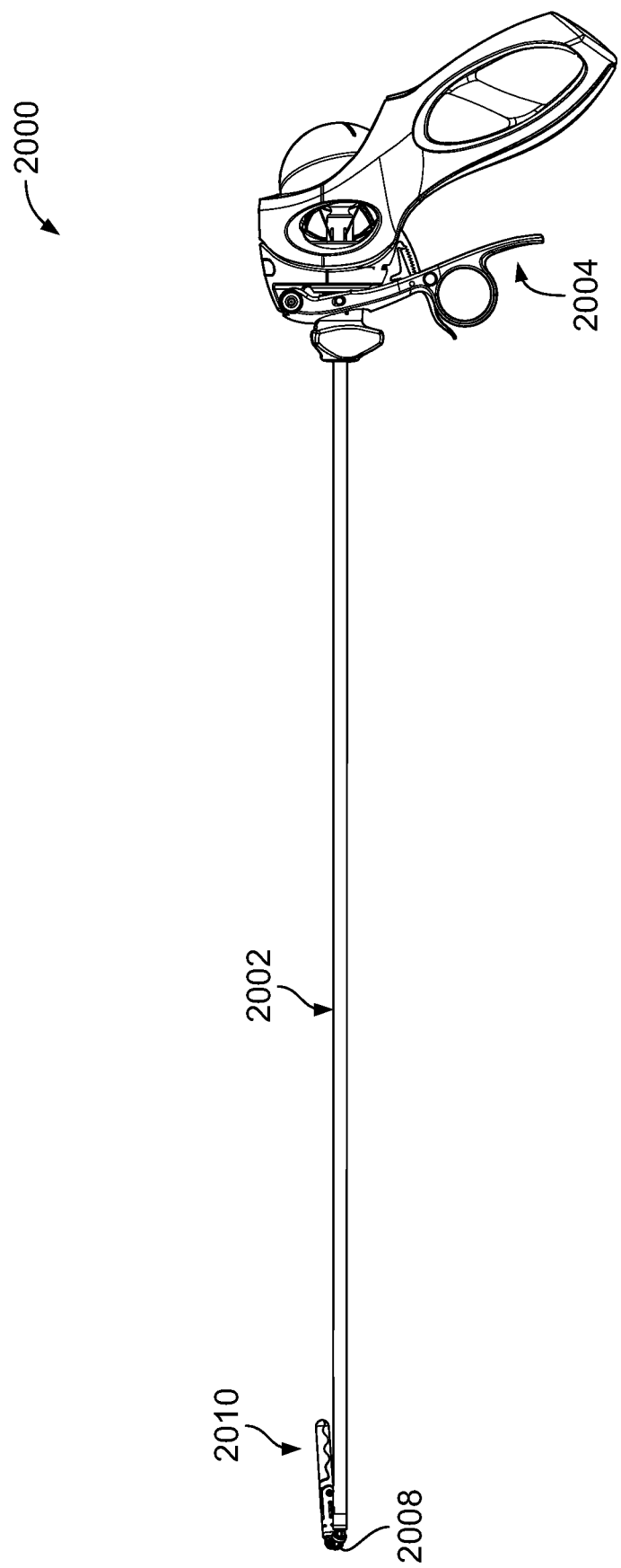
FIG. 27 is a side view of the laparoscopic device of FIG. 20, with the end effector in a different closed and bent configuration.

The latch mechanism 2028 can be locked at each valley 2066 of the ratchet rack 2046 to lock a corresponding open configuration of the end effector 2010 and can be unlocked (e.g., released or disabled) to adjust the extent to which the end effector 2010 is open. The end effector 2010 achieves a fully closed configuration (as shown in FIGS. 26 and 27) when the tooth 2048 of the ratchet finger 2036 is engaged with the inward-most tooth 2050 and valley 2066 of the ratchet rack 2046. The end effector 2010 achieves a fully open configuration (as shown in FIG. 20) when the tooth 2048 of the ratchet finger 2036 abuts the outer-most most tooth 2050 of the ratchet rack 2046. The ratchet defeat lever 2049 can be depressed to pivot the ratchet finger 2038 about the pin 2042 against the spring 2040 to lift the ratchet finger 2038 up from the ratchet rack 2046 such that the ratchet finger 2038, mounted to the lever 2026, can be moved outward or inward along the ratchet rack 2046. The ratchet defeat lever 2049 can be released to allow the ratchet finger 2036 to return to the spring-loaded position and locked at a desired position along the ratchet rack 2046.

Figure 31:
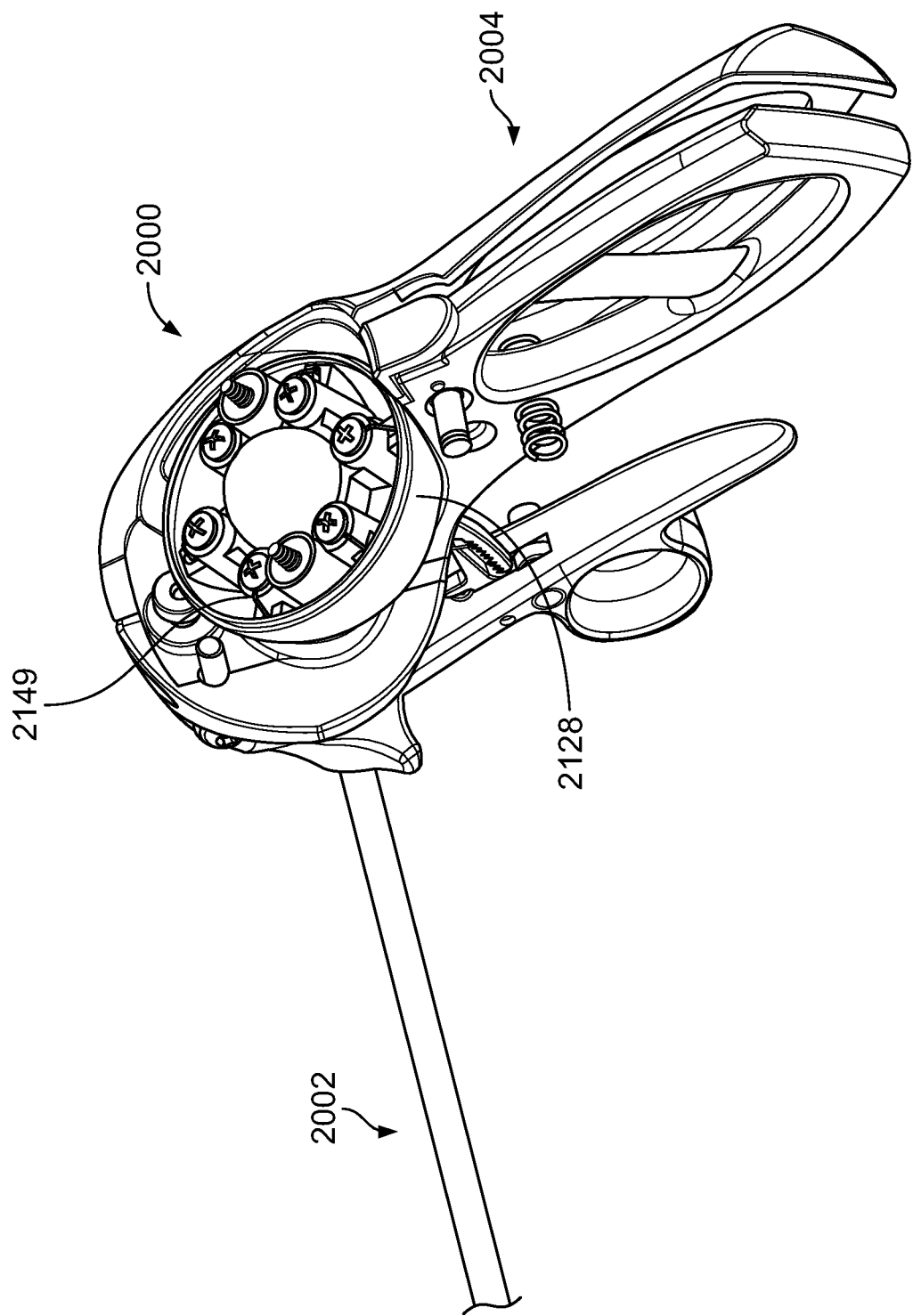
FIG. 31 is a perspective view of the proximal region of the laparoscopic device of FIG. 20, with certain outer components omitted to illustrate proximal ends of cables of the laparoscopic device.
Figure 32:
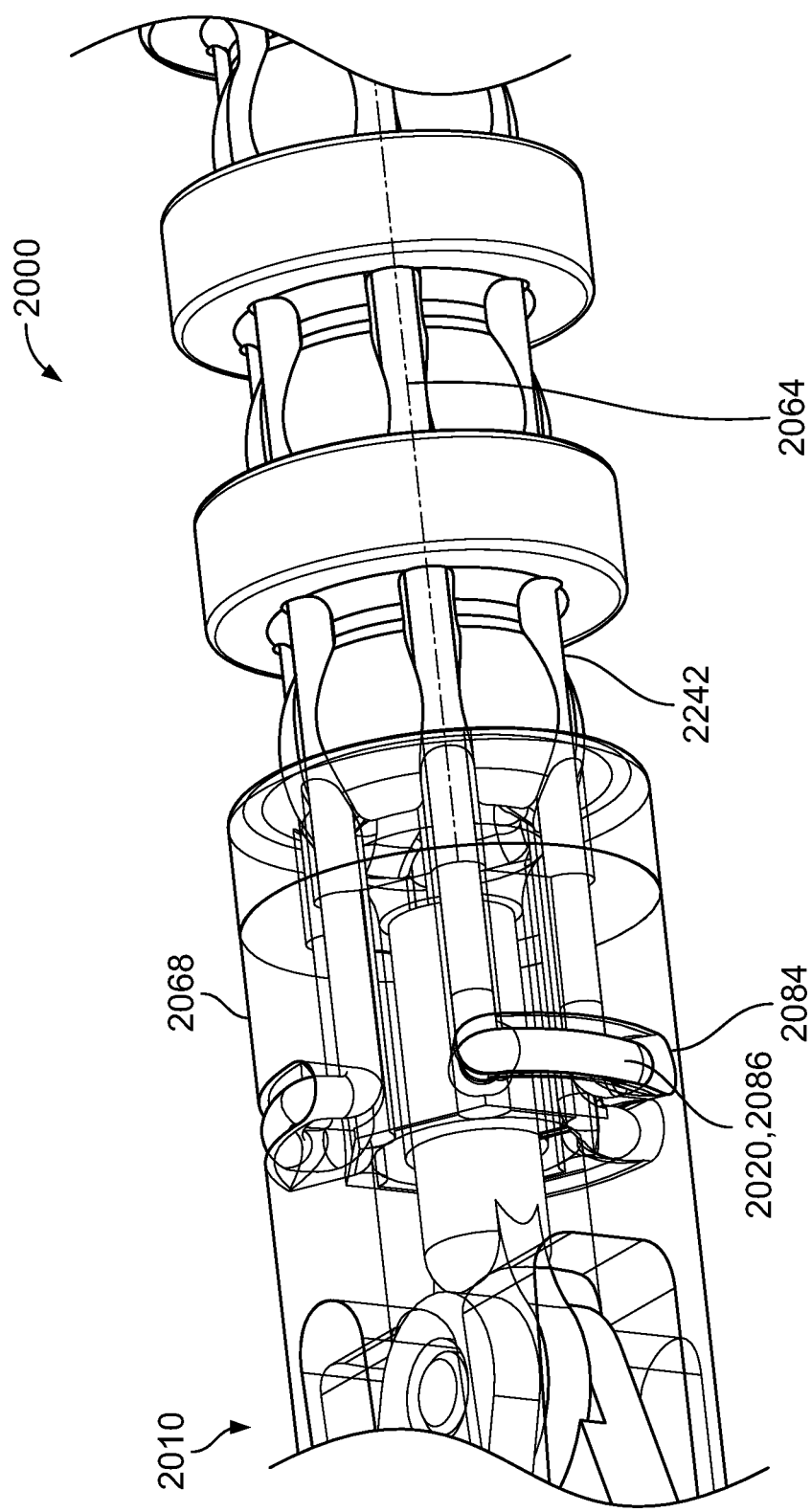
FIG. 32 is a perspective view of distal ends of the cables of the laparoscopic device of FIG. 20.

Referring to FIGS. 28 and 32, the end effector 2010 is similar in function to the end effector 1010 and includes a first jaw 2070 and a second jaw 2076 that are pivotable about axes defined by pin couplings. The end effector 2010 also includes a support base 2068 that is coupled to the articulation segment 2008, through which the distal wire section 2064 of the rod 2018 passes. Referring to FIGS. 31 and 32, the laparoscopic device 2000 includes three cables 2020 that respectively wrap around the support base 2068 at distal ends 2086 along circumferential channels 2084 of the support base 2068, thereby doubling back on each other and forming six cable portions 2242 that extend from the distal end to the proximal end of the laparoscopic device 2000. The cable portions 2242 are about equally spaced around a circumference of the shaft assembly 2002. At the proximal end of the laparoscopic device 2000, the cables 2020 wrap around a central region of the outer ball 2128 at their proximal ends 2149. The support base 2068 further defines a central slot along which the distal wire section 2064 of the rod 2018 can translate axially to pivot the jaws 2070, 2076 to open and close the end effector 2010. When the distal wire section 2064 is located at a distal-most position (e.g., when the lever 2026 of the trigger assembly 2024 is fully released at the spring-loaded configuration), the jaws 2070, 2076 are fully open, as shown in FIGS. 20 and 28. When the distal wire section 2064 is located at a proximal-most position (e.g., when the lever 2026 of the trigger assembly 2024 is fully depressed towards the grip body 2022), the jaws 2070, 2076 are fully closed, as shown in FIGS. 26 and 27.

The articulation segment 2008 is adjustable to allow the end effector 2010 to bend in all directions. The distal wire section 2064 is a thin, compliant section (e.g., a nitinol wire) that is malleable to bend within the articulation segment 2008 such that an extent to which the end effector 2010 is open or closed is independent of an orientation of a central axis of the support base 2068 with respect to a central axis of the shaft 2006. The articulation segment 2008 is substantially similar in construction and function to the articulation segment 1008. Accordingly, the articulation segment 2008 includes the proximal socket 1092, multiple of the central bearings 1096, and the distal ball component 1102. The balls 1098, 1102 respectively sit and are rotatable within the sockets 1092, 1100 to form multiple (e.g., four) ball-and-socket joints 1104 that together allow the articulation segment 2008 to bend such that the end effector 2010 can be articulated (e.g., bent) by up to about 180 degrees with respect to a central axis of the shaft 2006, as shown in FIGS. 26 and 27. The articulation segment 2008 may include a variable number of central bearings 1096 to allow the end effector 2010 to bend to varying extents.

The distal end portion 2094 of the shaft 2006, the proximal socket 1092, the central bearings 1096, and the distal ball component 1102 together define multiple (e.g., six) slots through which the cables 2020 extend proximally from the support base 2068 of the end effector 2010 into the shaft 2006. The slots are positioned along a circle that is concentric with the central axis 2090 of the shaft 2006 such that the cables 2020 are equally spaced radially from the central axis 2090 of the shaft 2006. The articulation segment 2008 includes the flexible sleeve 1108 (shown in FIGS. 1 and 3) that surrounds and covers the proximal socket 1092, the central bearings 1096, the distal ball component 1102, and the cables 2020. The cables 2020 further extend through the shaft 2006 and proximally into the outer ball 2128 of the track ball assembly 2016.

Referring to FIG. 22, the track ball assembly 2016 includes an inner ball 2114, a collar 2206 that rigidly connects the inner ball 2114 to the shaft 2006, and the outer ball 2128. The outer ball 2128 surrounds and is rotatable about the inner ball 2114 for rotation of the shaft assembly 2002 and articulation of the end effector 2010. The inner ball 2114 is generally spherical in shape. The outer ball 2128 is thumb-operated and is centered along the central axis 2090 of the shaft 2006. The outer ball 2128 defines multiple slots 2136 through which the cables 2020 pass and are attached to the track ball assembly 2016 at their proximal ends 2149.

The outer ball 2128 provides an ergonomic surface by which the track ball assembly 2016 can be manipulated (e.g., rotated about the central axis 2090 or pivoted laterally in any direction with respect to a centerpoint of the inner ball 2114) to manipulate the end effector 2010. In some embodiments, the outer ball 2128 may define a north cross hair and a south cross hair that indicate (e.g., correspond with) respective orientations of the first and second jaws 2070, 2076 so that a user who lacks direct vision of the end effector 2010 is aware of the orientations of the jaws 2070, 2076. The outer ball 2128 is typically made of one or more materials that facilitate tactile contact (e.g., gripping and compression) with the user's thumb, such as thermoplastic elastomers (TPE). Example materials can include styrenic block copolymer compounds (SBC or TPE-S), polyolefinic rubber blends (TPO or TPE-O), and thermoplastic vulcanizates (TPV or TPV-V), among others.

In the compressed configuration of the grip body 2022, the outer ball 2128 and the cables 2020 secured thereto are locked in position such that a rotational position of the shaft assembly 2002 and an articulated position (e.g., a degree of bending) of the end effector 2010 is also locked (e.g., fixed). In the expanded configuration of the grip body 2022, the outer ball 2128 can be rotated and pivoted within the round pocket 2170. Accordingly, the entire shaft assembly 2002 (e.g., with a fixed articulated position of the end effector 2010) can be rotated as a single unit about the central axis 2090 of the shaft 2006 by pivoting the outer ball 2128 left, right, up, down, or in any direction with respect to the inner ball 2114. Pivotable movement of the outer ball 2128 accordingly moves the proximal ends 2149 of the cables 2020 to effect bending of the end effector 2010 via the articulation segment 2008. The cables 2020 extend along a same side of the central axis 2090 of the shaft 2006 for an entire length of the cables 2020, such that each cable 2020 is located on same sides of the support base 2068 of the end effector 2010 and the outer ball 2128 and function in the manner as described with respect to the cables 1020 of the laparoscopic device 1000 to provide a "natural" articulation direction.

Figure 24:
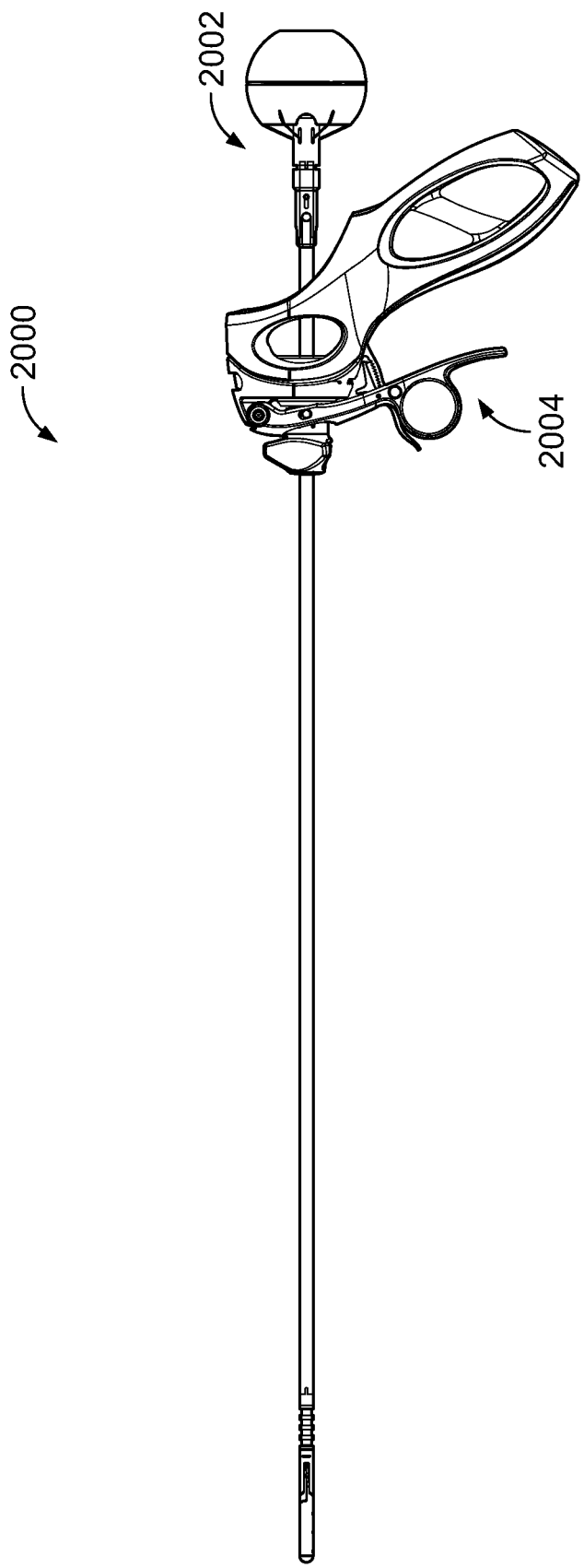
FIG. 24 is a side view of the laparoscopic device of FIG. 20 in a disassembled state.
Figure 25:
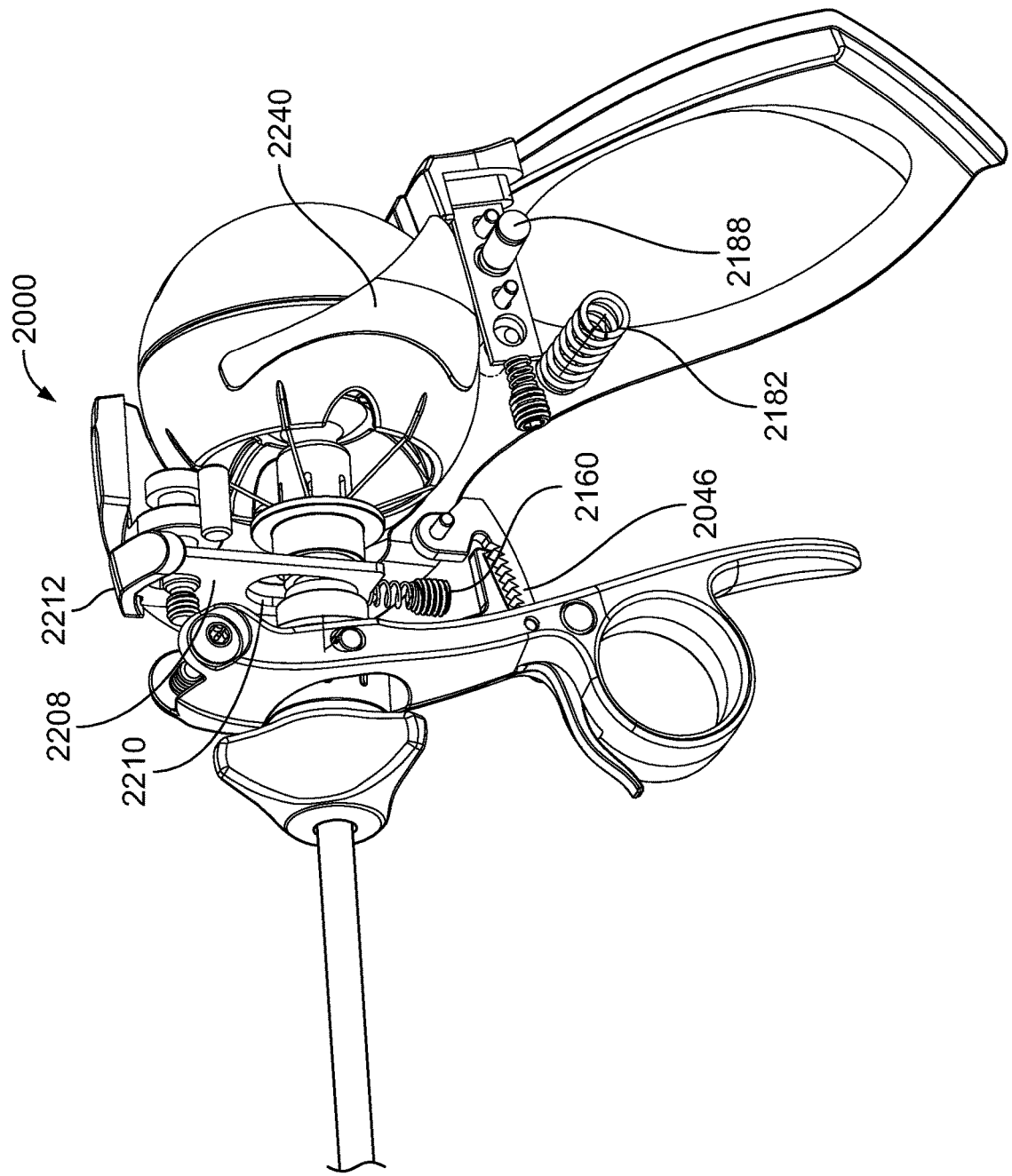
FIG. 25 is a perspective view of the proximal region of the laparoscopic device of FIG. 20, with certain outer components omitted to illustrate certain internal components.

Referring to FIGS. 22 and 25, the central portion 2178 of the grip body 2022 defines a slot 2158 in which a metal spring 2160 of the handle assembly 2004 is disposed. The central portion 2178 also carries a push button 2212 and a metal plate 2208 that is secured thereto. The metal plate 2208 defines an opening 2210 that is sized to allow passage of the shaft assembly 2002 for installing the shaft assembly 2002 to and removing the shaft assembly 2002 from the handle assembly 2004. The metal spring 2160 biases the push button 2212 to the position shown in FIGS. 22 and 25 such that the collar 2206 rests against (e.g., abuts) the metal plate 2208 within the opening 2210 to secure the shaft assembly to the handle assembly 2004. Alternatively, when the push button 2212 is depressed, the opening 2210 aligns with the collar 2206 such that the shaft assembly 2002 can pass through the opening 2210 to attach the shaft assembly 2002 to the handle assembly 2004 or remove the shaft assembly 2002 from the handle assembly 2004, as shown in FIG. 24.

The laparoscopic device 2000 is an ergonomic, easy-to-use, and intuitive tool that provides multiple functions. Such functions include opening and closing of the end effector 2010, locking and unlocking (e.g., releasing) of an open/closed configuration of the end effector 2010, articulation (e.g., bending) of the end effector 2010, locking and unlocking of an articulated configuration of the end effector 2010, rotation of the shaft assembly 2002, and removal and installation of the shaft assembly 2002. Furthermore, the laparoscopic device 2000 can exhibit more than one configuration respectively associated with these functions at the same time due to couplings among the component parts of the laparoscopic device, even while the functions can be executed independently of one another. For example, while the laparoscopic device 2000 can exhibit a "roticulated" configuration in which both the end effector 2010 is articulated (e.g., whether bent or in-line) with respect to the central axis 2090 of the shaft 2006 and in which the shaft assembly 2002 is rotated with respect to a nominal orientation, articulation of the end effector 2010 and rotation of the shaft assembly 2002 can be carried out independently of each other. Additionally, the jaws 2070, 2076 may be open or closed in any articulated position of the end effector 1010 and in any rotational position of the shaft assembly 2002.

In some embodiments, the shaft assembly 2002 is a disposable device that may be discarded after a single use. In some embodiments, the shaft assembly 2002 is a reusable device that may be disinfected between each of multiple uses. The shaft 2006 typically has a length of about 25 cm to about 50 cm (e.g., about 30 cm) and an outer diameter of about 3 mm to about 10 mm (e.g., about 3 mm or about 5 mm) such that the shaft 2006 can pass through trocars of standard sizes. The shaft 2006 is typically made of one or more materials, such as stainless steel. The cables 2020 are typically made of one or more compliant materials, such as stainless steel. The cables 2020 can withstand a tension of up to about 15 N to about 30 N. The cables 2020 typically have a total length of about 31 cm to about 56 cm (e.g., about 56 cm). The outer ball 2128 typically has a width of about 25 mm to about 60 mm (e.g., about 45 mm). The inner ball 2114 typically has a diameter of about 1 cm to about 3 cm (e.g., about 1.9 cm). Such a large width of the outer ball 2128 (e.g., compared to that of the outer ball assembly 1112) and a large diameter of the inner ball 2114 provides a greater extent (e.g., up to about 180 degrees) of articulation of the end effector 2010. Each outer portion 2180, 2200 of the grip body 2022 includes a patch 2240 of low durometer overmolded material (shown in FIG. 25) to increase friction between the outer portion 2180, 2200 and the outer ball 2128 during squeezing of the outer portions 2180, 2200 to lock rotation and articulation.

While the end effector 2010 has been illustrated as including the jaws 2070, 2076, in some embodiments, a laparoscopic device that is otherwise substantially similar in construction and function to the laparoscopic device 2000 may include a different type of end effector. Example end effectors include dissectors and graspers (e.g., Babcock, duckbill, 90 degrees, dolphin nose, fenestrated, flat nose, etc.), scissors (e.g., straight, Metz, curved, small mini, etc.), and needle holders (e.g., McKernan, Long jaw, etc.).

While the laparoscopic device 2000 has been described as including the pistol type grip body 2022, in some embodiments, a laparoscopic device that is otherwise similar in function to the laparoscopic device 2000 may alternatively include an in-line grip or a scissors grip.

Additionally, other embodiments and implementations are within the scope of the following claims.

What is claimed is:

1. A laparoscopic device, comprising:
an elongate shaft defining a central axis;
an end effector coupled to a distal end of the elongate shaft;
a rounded housing coupled to a proximal end of the elongate shaft, having a center point positioned along the central axis of the elongate shaft, and being pivotable to bend the end effector with respect to the central axis of the elongate shaft;
first and second cables extending from the end effector to the rounded housing respectively along a first side of the laparoscopic device and along a second side of the laparoscopic device disposed opposite the first side,
wherein the elongate shaft, the end effector, the rounded housing, and the first and second cables together form a shaft assembly for which the rounded housing is rotatable in fixed relation to the elongate shaft, the first and second cables, and the end effector; and
a handle comprising a trigger assembly and a grip body configured to support a hand for grasping the laparoscopic device, the grip body comprising first and second gripping members respectively positioned along the first and second sides of the laparoscopic device, and the grip body being adjustable between:
an expanded configuration in which the first and second gripping members are coupled to each other and spaced apart from the rounded housing to permit rotation of the rounded housing for rotating the shaft assembly with respect to the central axis of the elongate shaft and to permit pivoting of the rounded housing for bending the end effector with respect to the central axis of the elongate shaft, and
a compressed configuration in which the first and second gripping members compress the rounded housing to lock the rounded housing in a fixed position with respect to the grip body.

2. The laparoscopic device of claim 1, further comprising a bendable segment that couples the elongate shaft to the end effector.

3. The laparoscopic device of claim 2, wherein the bendable segment comprises a plurality of ball-and-socket joints.

4. The laparoscopic device of claim 2, further comprising a rod that extends from the proximal end of the shaft to the end effector and that is configured to effect opening and closing of the end effector based on axial movement of the rod.

5. The laparoscopic device of claim 4, wherein the rod comprises a compliant portion that passes through the bendable segment such that an open or closed configuration of the end effector is independent of the orientation of the end effector with respect to the central axis of the shaft and independent of a rotational orientation of the shaft assembly.

6. The laparoscopic device of claim 1, further comprising an interior ball about which the rounded housing is rotatable.

7. The laparoscopic device of claim 6, wherein the interior ball and the rounded housing together form a track ball assembly.

8. The laparoscopic device of claim 6, further comprising a collar that extends from the interior ball and that is rigidly attached to the proximal end of the elongate shaft to couple the rounded housing to the elongate shaft.

9. The laparoscopic device of claim 6, wherein the rounded housing defines a substantially spherical pocket.

10. The laparoscopic device of claim 1, wherein the grip body further comprises:

a central handle member disposed between the first and second gripping members, and a locking mechanism supported on the central handle member and configured to maintain the first and second gripping members in the compressed configuration of the grip body.

11. The laparoscopic device of claim 10, wherein the grip body further comprises a lock release mechanism supported on the central handle member and configured to release the first and second gripping members from the compressed configuration to the expanded configuration of the grip body.

12. The laparoscopic device of claim 1, further comprising a plurality of additional cables.

13. The laparoscopic device of claim 1, wherein the shaft assembly is selectively separable as an assembled unit from the handle.

14. The laparoscopic device of claim 13, wherein the handle further comprises a movable plate defining an opening sized for passage of the shaft assembly to permit installation of the shaft assembly to the handle and to permit removal of the shaft assembly from the handle.

15. The laparoscopic device of claim 1, wherein the handle comprises a ratcheting mechanism by which an open or closed configuration of the end effector can be locked and unlocked.

16. The laparoscopic device of claim 1, wherein the rounded housing is rotatable about any axis intersecting the center point of the rounded housing to move the first and second cables axially in opposite directions along the central axis of the elongate shaft to bend the end effector with respect to the central axis of the elongate shaft while the grip body is in the expanded configuration.

17. The laparoscopic device of claim 1, wherein the rounded housing is rotatable to rotate the shaft assembly with respect to the central axis of the elongate shaft with any orientation of the end effector with respect to the central axis of the elongate shaft while the grip body is in the expanded configuration.

18. The laparoscopic device of claim 1, wherein the grip body is biased to the expanded configuration.

19. The laparoscopic device of claim 1, wherein the rounded housing has a substantially spherical profile.

* * * * *